(12) United States Patent
Patil et al.

(10) Patent No.: US 9,827,325 B2
(45) Date of Patent: *Nov. 28, 2017

(54) DRUG DELIVERY OF TEMOZOLOMIDE FOR SYSTEMIC BASED TREATMENT OF CANCER

(71) Applicant: CEDARS-SINAI MEDICAL CENTER, Los Angeles, CA (US)

(72) Inventors: Rameshwar Patil, Los Angeles, CA (US); Eggehard Holler, Los Angeles, CA (US); Keith L. Black, Los Angeles, CA (US); Julia Y. Ljubimova, Studio City, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/450,519

(22) Filed: Mar. 6, 2017

(65) Prior Publication Data
US 2017/0274085 A1 Sep. 28, 2017

Related U.S. Application Data

(63) Continuation of application No. 15/054,266, filed on Feb. 26, 2016, now Pat. No. 9,629,919, which is a continuation of application No. 14/179,195, filed on Feb. 12, 2014, now Pat. No. 9,320,807, which is a continuation of application No. 13/513,145, filed as application No. PCT/US2010/059919 on Dec. 10, 2010, now Pat. No. 8,785,371.

(60) Provisional application No. 61/285,495, filed on Dec. 10, 2009.

(51) Int. Cl.
| | | |
|---|---|---|
| A61K 47/48 | (2006.01) | |
| C07K 16/28 | (2006.01) | |
| C07K 16/30 | (2006.01) | |
| A61K 31/4188 | (2006.01) | |
| A61K 31/425 | (2006.01) | |

(52) U.S. Cl.
CPC ........ *A61K 47/482* (2013.01); *A61K 31/4188* (2013.01); *A61K 31/425* (2013.01); *A61K 47/48061* (2013.01); *A61K 47/48215* (2013.01); *A61K 47/48246* (2013.01); *A61K 47/48338* (2013.01); *A61K 47/48384* (2013.01); *A61K 47/48561* (2013.01); *A61K 47/48584* (2013.01); *A61K 47/48623* (2013.01); *A61K 47/48669* (2013.01); *A61K 47/48692* (2013.01); *C07K 16/2881* (2013.01); *C07K 16/3015* (2013.01); *C07K 16/3053* (2013.01); *C07K 2317/24* (2013.01); *C07K 2317/77* (2013.01)

(58) Field of Classification Search
None
See application file for complete search history.

(56) References Cited

U.S. PATENT DOCUMENTS

| | | |
|---|---|---|
| 6,472,512 B1 | 10/2002 | Lafleur et al. |
| 7,056,532 B1 | 6/2006 | Kabanov et al. |
| 7,056,704 B2 | 6/2006 | Tuschl et al. |
| 7,332,585 B2 | 2/2008 | Adams et al. |
| 7,618,626 B2 | 11/2009 | Gualberto et al. |
| 7,935,677 B2 | 5/2011 | Ljubimova et al. |
| 8,309,614 B2 | 11/2012 | Ding et al. |
| 8,562,964 B2 | 10/2013 | Ljubimova et al. |
| 8,785,371 B2 | 7/2014 | Patil et al. |
| 8,795,648 B2 | 8/2014 | Ding et al. |
| 8,911,717 B2 | 12/2014 | Ljubimova et al. |
| 9,320,807 B2 | 4/2016 | Patil et al. |
| 9,623,041 B2 | 4/2017 | Inoue et al. |
| 9,629,919 B2 | 4/2017 | Patil et al. |
| 2002/0155440 A1 | 10/2002 | Ljubimova et al. |
| 2005/0187206 A1 | 8/2005 | Adin et al. |
| 2007/0259008 A1 | 11/2007 | Ljubimova et al. |
| 2009/0263331 A1 | 10/2009 | Wu et al. |

FOREIGN PATENT DOCUMENTS

| | | |
|---|---|---|
| CN | 1615855 A | 5/2005 |
| KR | 20070036130 A | 4/2007 |
| WO | WO-9909045 A1 | 2/1999 |
| WO | WO-0187239 A2 | 11/2001 |
| WO | WO-02059610 A2 | 8/2002 |
| WO | WO-2005028617 A2 | 3/2005 |
| WO | WO-2005055980 A2 | 6/2005 |
| WO | WO-2009126913 A1 | 10/2009 |
| WO | WO-2011072240 A1 | 6/2011 |

OTHER PUBLICATIONS

Abdellaoui et al. Metabolite-derived Artificial Polymers Designed for Drug Targeting, Cell Penetration and Bioresorption, European Journal of Pharmaceutical Sciences, vol. 6, No. 1 (1998), pp. 61-73.

(Continued)

*Primary Examiner* — Robert A Wax
*Assistant Examiner* — Randeep Singh
(74) *Attorney, Agent, or Firm* — Wilson Sonsini Goodrich & Rosati

(57) ABSTRACT

The present invention relates to methods of drug delivery for the treatment of a condition or disease, such as cancer. In one embodiment, the invention provides a method of preparing a multifunctional nanoconjugate of temozolomide (TMZ) by conjugating TMZ in its hydrazide form to a polymalic acid platform. In another embodiment, the polymalic acid platform is conjugated to a monoclonal antibody to transferrin receptor, a trileucine (LLL) moiety, and/or a polyethylene glycol (PEG) moiety. The present invention relates to methods of drug delivery for the treatment of a condition or disease, such as cancer. In one embodiment, the invention provides a method of preparing a multifunctional nanoconjugate of temozolomide (TMZ) by conjugating TMZ in its hydrazide form to a polymalic acid platform. In another embodiment, the polymalic acid platform is conjugated to a monoclonal antibody to transferrin receptor, a trileucine (LLL) moiety, and/or a polyethylene glycol (PEG) moiety.

18 Claims, 13 Drawing Sheets

(56) References Cited

OTHER PUBLICATIONS

Agrawal et al., Anntisense Therapeutics: Is It As Simple As Complimentary Base Recognition?, Molecular Medicine Today, (Feb. 2000), pp. 72-81, 6.

Akbar, et al. Delivery of temozolomide to the tumor bed via biodegradable gel matrices in a novel model of intracranial glioma with resection. Journal of Neuro-Oncology 94 (2009): 203-212.

Albini et al. A rapid in Vitro Assay for Quantitating the Invasive Potentia of Tumor Cells, Cancer Research, (Jun. 15, 1997), pp. 3239-3245, 47(12).

Andrews et al. Resultes of a Pilot Study Involving the Use of an Antisense Oligodeoxynucleotide Directed Against the Insulin-like Growth Factor Type I Receptor in Malignant Astrocytomas, Journal of Clinical Oncology, (Apr. 15, 2001), pp. 2189-2200, 19(8).

Arora et al. c-Myc Antisense Limits Rat Liver Regeneration and Indicates Role for c-Myc in Regulating Cytochrome P-450 3A Activity, Kournal of Pharmacology and Experimental Therapeutics, (Mar. 2009), pp. 921-928, 292(3).

Arrowsmith, et al. Part 39 synthesis of bis(imidazotetrazine)s with saturated spacer groups.Journal of the Chemical Society 1. 24 (2000): 4432-4438.

Asthagiri, et al. Advances in brain tumor surgery. Neurologic Clinics 25 (2007): 975-1003.

Astriab-Fisher et al. Antisense Inhibition of P-Glycoprotein Expression Using Peptide- Oligonucleotide Conjugates, Biochemical Pharmacology (Jul. 1, 200), pp. 83-90, 60(1).

Auger, et al. Genetic alterations associated with acquired with temozolide resistance in Snb- 19, a human glioma cell line. Molecular Cancer Therapeutics 5 (2006): 2182-2192.

Barbosa et al. Investigation of the Degradation Mechanism of Poly(malic acid) Esters in Vitro and their Related Cytotoxicities on J774 Macrophages, Biomacromolecules 2004, vol. 5, No. 1, pp. 137-143.

Basye, et al. Triplex formation by morpholino oligodeoxyribonucleotides in the HER-2/neu promoter requires the pyrimidine motif. Nucleic Acids Research, 29 (2001): 4873-4880.

Belkin et al. Integrins as Receptors for Laminins, Microscopy Research and Technique, (Nov. 1, 2000), pp. 280-301, 51(3).

Bello et al., Simultaneous Inhibition of Glioma Angiogenesis, Cell Proliferation, and Invasion by a Naturally Occurring Fragment of Human Metalloproteinase-2, Cancer Research, (Dec. 15, 2001), pp. 8730-8736, 61(24).

Bickel et al., Delivery of Peptides and Proteins Through the Blood-Brain Barrier, Advanced Drug Delivery Reviews, (2001), pp. 247-279, 46.

Boado et al. Antisense-Mediated Down-Regulation of the Human Huntingtin Gene, Journal of Pharmacology and Experimental Therapy, (Oct. 200), pp. 239-243, 295(1).

Boado et al., Drug delivery of Antisense Molecules to the Brain for Treatemnet of Alzheimer's Disease and Cerebral Aids, Journal of Pharmacological Science, (1998), pp. 1308-1315, 87.

Braun, et al. Treatment glioblastoma multiforme cells with temozolomide-BioShuttle ligated by the inverse Diels-Aider ligation chemistry. Drug Design, Development and Therapy, Dove Medical Press Ltd, UK, 2008.2 (2009): 289-301.

Brem, et al. Local delivery of temozolomide by biodegradable polymers is superior to oral administration in a rodent glioma model. Cancer Chemother Pharmacol. 60 (2007): 643-650.

Broadwell et al., Transcytosis of Protein Through the Mammalian Cerebral Epithelium and Endothelium III Receptor-Mediated Transcytosis Through the Blood-Brain of Blood-Bome Transferrin and Antibpdy Against the Transferrin Receptor, Experimental Neurology, (1996), pp. 47-65, 142.

Bulmus et al., A new pH-Responsive and Glutathione-reactive Endosomal Membrane-disruptive Polymeric Carrier for Intracellular Delivery of Biomolecular Drugs, Journal of Controlled Release, (2003), 93: 105-120.

Cammas et al., Polymers of Malic Acid and 3-Akylmalic Acid as Synthetic PHAs in the Design of Biocompatible Hydrolyzable Devices, International Journal of Biological Macromolecules, (1999), pp. 273-282, 25.

Carlsson, et al. Protein thiolation and reversible protein-protein conjugation. N-Succinimidyl 3-(2-pyridyldithio)propionate, a new heterobifunctional reagent. Biochem J. Sep. 1, 1978;173(3):723-737.

CBTRUS Statistical Report 2009 : Primary Brain and Central Nervous System Tumors Diagnosed in the united States in 2004-2005. http://www.cbtrus.org/reports/2009-NPCR-04-05/CBTRUS-NPCR2004-2005-Report-.pdf (accessed (Nov. 17, 2009).

Chen, et al. Of *escherichia coli* and man: understanding glioma resistance to temozolmide therapy. In E. G. Meir (eds.), CN8 Cancer, Humana Press, Atlanta, (2009): 679-711.

Colognato et al., Form and Function: The Laminin Family of Heterotrimers, Developmental Dynamics, (Jun. 2000), pp. 213-234, 218(2).

Coonrad, et al. On the mechanism of DNA transfection: efficient gene transfer without viruses, Gene Therapy, 4 (1997): 1313-1321.

Co-pending U.S. Appl. No. 15/447,439, filed Mar. 2, 2017.

De Diesbach et al.,Identification, Purification and Partial Charaterozation of An Oligonucleotide Receptor in Membranes of HepG3 Cells, Nucleic Acids Research, (Feb. 15, 2000), pp. 868-874, 28(4).

Dias et al., Antisense Oligonucleotides: Basic Concepts and Mechanisms, Molecular Cancer Therapy, (Mar. 2002), pp. 3470355, 1(15).

Ding et al., HER2-positive breast cancer targeting and treatment by a peptide-conjugated mini nanodrug, Nanomedicine: Nanotechnology, Biology, and Medicine, 13: 631-639 (2017).

Duncan, et al. Polymer-drug conjugates: towards a novel approach for the treatment of endrocine-related cancer. Endocrine-Related Cancer, 12 (2005): S189-S199.

Duncan. The dawning era of polymer therapeutics. Nat. Rev. Drug Discovery 2:347-360 (2003).

EP10836765.7 Extended European Search Report dated Oct. 9, 2013.

European search report dated Feb. 7, 2014 for EP10861515.

European search report with written opinion dated Jan. 4, 2013 for EP09730249.

Ferrari. Cancer nanotechnology: opportunities and challenges. Nat Rev Cancer 5:161-171 (2005).

Final Office action dated Sep. 8, 2013 for U.S. Appl. No. 13/513,145.

Final Office action dated Oct. 29, 2015 for U.S. Appl. No. 13/930,533.

Fischer et al., An Unusual Polyanion From Physarum Polycephalum That Inhibits Homologoes DNA Polymerase A In Vitro, Biochemistry, (1989), pp. 5219-5226, 28.

Friedman, et al. Temozolomide and treatment of malignant glioma. Clin Cancer Res. Jul. 2000;6(7):2585-97.

Fu, et al. Calcein permeability of liposomes mediated by type A botulinum neurotoxin and its light and heavy chains. Journal of protein chemistry 18 (1999): 701-707.

Fujita, et al. Brain tumor tandem targeting using a combination of monoclonal antibodies attached to biopoly(beta- L-malic acid), Journal of Controlled Release, 122.3 (2007): 356-363.

Fujita et al., Inhibition of Laminin-8 In Vivo Using a Novel Poly(Malic Acid)-Based Carrier Reduces Glioma Angiogenesis, Angiogenesis, (2006), pp. 183-191.

Fujita, et al. Overexpression of beta1-chain-containing lam in ins in capillary basement membranes of human breast cancer and its metastases, Breast Cancer Research, vol. 7, No. 4, p. R411-R421 (Apr. 6, 2005) Retrieved from the Internet<URL:http://breast-cancer-research.com/contenU7/4/R411>.

Fujiwara et al., Purification and Characterization of Human Laminin-8 Stimulates Cell Adhesion and Migration Through a3p1 and a6p Integrins, Journal of Biological Chemistry, (May 18, 2001), pp. 17550-17558, 276(20),.

Fukushima et al. Integrin a3(31-mediated Interaction with Laminin-5 Stimulates Adhesion, Migration and Invasion of Malignant Glioma Cells, Int. Journal of Cancer (Mar. 30, 1998), 76(1), pp. 63-72.

(56) References Cited

OTHER PUBLICATIONS

Gewirtz et al., Facilitating Oligonucleotide Delivery: Helping Antisense Deliver on Its Promise, Proceedings of the National Academy of Sciences of USA, (Apr. 1996), pp. 3161-3163, 93.
Gonzales et al., Complex Interactions Between the Laminin a4 Subunit and Integrins Regulate Endothelial Cell Behaviour In Vitro and Angiogenesis In Vivo, Proceedings of the National Academy of Sciences USA, (Dec. 10, 2002), pp. 16075-16080, 99(25).
Hayashi et al., Identification and Recombination Production of Human Laminin a4 Subunit Splice Variants, Biochemical and Biophysical Research Communications, (Dec. 6, 2002), pp. 498-504, 299(3).
Herold-Mende et al. Clinical Impact and Functional Aspects of Tenascin-C Expression During Glioma Progression, International Journal of Cancer, (Mar. 20, 2002), pp. 362-369, 98(3).
Holler, Poly(malic acid) from natural sources. In N. P. Cheremisinoff (eds.), Handbook of Engineering Polymeric Materials, Marcel Dekker, New York, 1997, 93-103.
Hui, et al. Inhibition of brain tumor growth by intravenous poly (-L-malic) acid nanobioconjugate with pH- dependent drug release; Proceedings of the National Academy of Sciences, Correction in vol. 107, No. 45, p. 19603 (Nov. 9, 2010).
Hui, et al. Inhibition of brain tumor growth by intravenous poly (-L-malic) acid nanobioconjugate with pH- dependent drug release; Proceedings of the National Academy of Sciences, vol. 107, No. 42, pp. 18143-18148 (Oct. 19, 2010).
Inoue e ta., Polymalic Acid—Based Nanobiopolymer Provides Efficient Systemic Breast Cancer Treatment by Inhibiting both HER2/neu Receptor Synthesis and Activity, Cancer Res; 71(4):1454-1464 (2011).
Inoue, et al. Newly designed nanobioconjugate for direct targeting and systemic treatment of HER2- positive breast cancer, Proceedings of the American Association for Cancer Research Annual Meeting, 101st Annual Meeting of the American Association for Cancer Research, Washington, D.C. vol. 51, p. 937 (Apr. 17-21, 2010).
International search report with written opinion dated Feb. 11, 2011 for PCT/US2010/059919.
International search report with written opinion dated Jul. 14, 2009 for PCT/US2009/040252.
International search report with written opinion dated Oct. 25, 2011 for PCT/US2010/062515.
Iversen, et al. Efficacy of antisense morpholino oligomer targeted to c-myc in prostate cancer xenograft murine model and a Phase I safety study in humans. Clinical Cancer Research, 9 (2003): 2510-2519.
Iwata et al., A Novel Surgical Glue Composed of Gelatin and N-Hydroxysuccinimide Activate Poly(L-Glutamic Acid): Part 1 Synthesis of Activated Poly(L-Glutamic Acid) and Its Gelation With Gelatin, Biomaterials, (1998), pp. 1859-1876, 19.
Jansen et al., Chemosensitisation of Malignant Melanoma by BCL2 Antisense Therapy, Lancet, (Nov. 18, 2000), pp. 1728-1733, 356(9243).
Kabanov, et al. Polymer genomics: shifting the gene and drug delivery paradigms. Journal of Controlled Release 101 (2005): 259-271.
Kachra et al. Expression of Matrix Metalloproteinases and Their Inhibitors in Human Brain Tumors, Clinical and Experimental Metastasis, (1999), pp. 555-566, 17(7).
Khazenzon et al., Antisense Inhibition of Laminin-8 Expression Reduces Invasion of Human Gliomas In Vitro, Molecular Cancer Therapeutics, (2003), pp. 985-994,2.
Khazenzon et al., Novel Angiogenic Targets for Human Glioma Prevention and Regulation of Their Expression, International Journal of Molecular Medicine, 2002, 10:Supplementa 1, p. S41, XP008091390.
Kitange, et al. Induction of MGMT expression is associated with temozolomide resistance in glioblastoma xenografts. Journal of Neuro-Oncology. 11: (2009) 281-291.
Kleinman et al., Basement Membrane Complexes with Biological Activity, Biochemistry, (Jan. 28, 2986), pp. 312-318, 25(2).
Knott et al., Stimulation of Extracellular Matrix Components in the Normal Brain by Invading Glioma Cells, International of Cancer, (Mar. 16, 1998), pp. 864-872, 75(6).
Komata et al., Combination Therapy of Malignant Glioma Cells With 2-5A-Antisense Telomerase RNA and Recombinant Adenovirus p53, Gene Therapy, (Dec. 2000), pp. 20171-2079, 7(24).
Kondraganti et al., Selective Supression of Matrix Metalloproteinase-9 in Human Glioblastoma Cells by Antisense GeneTransfer Impairs Glioblastoma Cell Invasion, Cancer Research, (Dec. 15, 2000), pp. 6851-6855, 60(24).
Kopecek et al., HPMA Copolymer -Anticancer Drug Conjugates: Design, Activity, and Mechanism of Action, european Journal of Biopharmacology, (2000), pp. 61-81, 50.
Korherr et al., Poly ((3-1 Malate) Hydrolase From Plasmodia of Physarum Polycephalum, Canadian Journal of Microbioligy, (1995), pp. 192-199, 41 (Suppl. 1).
Kramerov et al., Inhibition of Protein Kinase CK2 Suppresses Angiogenesis and Hematopoietic Stem Cell Recruitment to Retinal Neovascularization Sites. Molecular and Cellular Biochemistry 316:177-186, 2008.
Kulla et al., Tenascin Expression Patterns and Cells of Monocyte Lineage: Relationship in Human Gliomas, Moder Pathology, (Jan. 2000), pp. 58-67, 13(1).
Kurihara et al., Epidermal Growth Factor Radiopharmaceuticals:111m Cheladon, Conjugation to a Blood-Brain Barrier Delivery Vector Via a Biotin-Polyethylene Linker, Pharmacokinetics, and In Vivo Imaging of Experimental Brain Tumors, Bioconjugate Chemistry, (1999), 505-511, 10.
Lacera et al., Restoration of Hemaglobin a Synthesis in Erythroid Cells From Peripheral Blood of Thalassemic Patients, Proceedings of the National Academy of Sciences USA, (Aug. 15, 2000), pp. 9591-9596, 97(17).
Lacroix, et al. A multivariate analysis of 416 patients with glioblastoma multiforme: prognosis, extent of resection, and survival. Journal of Neurosurgery 95 (2001): 190-198.
Lal et al., A Public Database for Gene Expression in Human Cancers, Cancer Research, (Nov. 1, 1999), pp. 5403-5407, 59(21).
Lee, et al. Delivery of antisense oligonucleotides and transferrin receptor antibody in vitro and in vivo using a new multifunctional drug delivery system based on polymalic acid, Proceedings of the American Association for Cancer Research, 45 (2004), Abstract #647.
Lee et al., Effects of Culture Conditions on p-Poly(I-Malate) Production by Physarum Polycephalum, Applied Microbiology and Biotechnology, (1999), pp. 647-652, 51.
Lee, et al. Polycefin, a New Prototype of a Multifunctional Nanoconjugate Based on Poly(B-L-malic acid for Drug Delivery, Bioconjugate Chemistry, 17.2 (2006): 317-326.
Ljubimov et al. Human Corneal Basement Membrane Heterogeneity, Topographical Differences in the Expression of Type IV Collagen and Laminin Isoforms, Lab Invetsigation, (Apr. 1995), pp. 461-473, 72(4).
Ljubimova et al. A new Multifunctional Drug Delivery System Based on Polymalic Acid to Inhibit Angiogenesis and Invasion of Human Gliomas In Vitro and In Vivo, European Journal of Cancer, Supplement, 2004, 2:8, p. 184. XP004640052.
Ljubimova et al., Changes in Laminin Isoforms Associated with Brain Tumor Invasion and Angiogenesis, Frontiers in Bioscience, (Jan. 1, 2006), vol. 11, pp. 81-88.
Ljubimova et al. Development of an In Vitro System to Block the Angiogenic Target, Laminin-8, in Human Gliomas, Proceedings of the American Association for Cancer Annual Meeting, Mar. 2002, vol. 43, p. 177, XP001536931.
Ljubimova et al., Development of Anti-Angiogenic and Anti-Invasive Inhibitors of Human Gliomas Using a New Multifunctional Drug delivery System Based on Polymakic Acid, Preclinica (Sep./Oct./2004), 2(5), p. 366.
Ljubimova et al., Gene Array Analysis of Differentially Expressed Genes in Human Glial Tumors, International Journal of Oncology, (2001), pp. 287-295, 18.

(56) References Cited

OTHER PUBLICATIONS

Ljubimova, et al. Nanoconjugate based on polymalic acid for tumor targeting, Chemico-Biological Interactions, 171.2 (2008): 195-203.
Ljubimova et al., Overexpression of a4 Chain-Containing Laminins in Human Glial Tumors Identified by Gene Microarray Analysis, Cancer Research (Jul. 15, 2001), pp. 5601-5610, 61(14).
Ljubimova, J. et al., Association between Laminin-8 and Glial Tumor Grade, Recurrence, and Patient Survival, Cancer (online Jun. 16, 2004), 101(3), pp. 604-612.
Ljubimova, Julia Y. et al. Molecular Oncology; Internet citation, XP008143608 (Jul. 1, 2009). Retrieved from the Internet:URL:http://www.cedars-sinai.edu/10141.html (retrieved on Sep. 29, 2011).
Ljubimova, Julia Y. et al. Poly( malic acid) nanoconjugates containing various antibodies and oligonucleotides for multitargeting drug delivery, Nanomedicine, 3.2 (2008): 247-265.
Lorenz, et al. Uptake of functionalized, fluorescent-labeled polymeric particles in different cell lines and stem cells. Biomaterials. 27 (2006): 2820-2828.
Louis, et al. The 2007 WHO classification of tumours of the central nervous system. Acta Neuropathol. 114 (2007): 97-109.
Lu et al., Delivering siRNA In Vivo for Functional Genomics and Novel Therapeutics, RNA Interference Technology, (2205), pp. 303-317.
Lutsenko, et al. Biochemical Basis of Regulation of Human Copper-Transporting ATPases, Archives of Biochemistry and Biophysics, 463.2 (2007): 134-148.
MacDonald et al., Urokinase Induces Receptor Mediated Brain Tumor Cell Migration and Invasion, Journal of Neuro Oncology, (Dec. 1998), pp. 215-226, 40(3).
Machine translation of CN1615855A, 2005, 4 pages.
Maeda et al. Vascular permeability enhancement in solid tumor: various factors, mechanisms involved and its implications. International Immunopharmacology 3:319-328 (2003).
McKean et al., FAK Induces Expression of Prx1 to Promote Tenascin-C-Dependent Fibroblast Migration, Journal of Cell Biology, (Apr. 28, 2003), pp. 393-402, 161(2).
Minakawa et al., In Vitro Interaction of Astrocytes and Pericytes With Capillary-Like Structures of Brain Microvessel Endothelium, Lab Investigation, (Jul. 1991), pp. 32-40, 65(1).
Miner et al. The Laminin Alpha Chains: Expression, Developmental Transitions, and Chromosomal Locations of A1-5, Identification of Heterotrimeric Laminins 8-11, and Cloning of a Novel a3 Isoform, Journal of Cell Biology, (May 5, 1997), pp. 685-701, 137(3).
Mosmann. Rapid colorimetric assays for cellular growth and survival: application to proliferation and cytotoxicity assays. Journal of Immunological Methods. 65 (1983): 55-63.
Nagato et al., Downregulations of Laminin a-4 Chain Expression Inhibits Glioma Invasion In Vitro and In Vivo, Int. Journal of Cancer (onlune Jun. 16, 2004), pp. 604-612.
NCBI GenBank Accession No. NM_002291 (Nov. 21, 2010)—See the whole document.
NCBI GenBank Accession No. NM_005228 (Dec. 26, 2010)—See the whole document.
NCBI GenBank Accession No. X03363 (Mar. 30, 1995)—See the whole document.
NCBI GenBank Accession No. X91171 (Oct. 7, 2008)—See the whole document.
NCBI GenBank ATP7B [*Homo sapiens*] AAB52902.1 (1997): 3 pages.
Nel, et al. Understanding biophysicochemical interactions at the nano-bio interface. Nature Materials. 8 (2009): 543-557.
Nielsen et al., Peptide Nucleic Acid Targeting of Double-Stranded DNA. Methods in Enzymology, 2001, pp. 329-340, 340.
Nielsen P.E. The Last Hurdle?, Gene Therapy, (2005), pp. 956-957, 12.
Non-Final Office action dated Apr. 4, 2016 for U.S. Appl. No. 15/054,266.
Non-Final Office action dated Aug. 27, 2015 for U.S. Appl. No. 14/179,195.
Non-Final Office action dated Nov. 4, 2012 for U.S. Appl. No. 12/935,110.
Non-Final Office action dated Mar. 14, 2013 for U.S. Appl. No. 13/513,145.
Non-Final Office action dated Oct. 15, 2014 for U.S. Appl. No. 13/930,533.
Non-Final Office action dated Jun. 18, 2015 for U.S. Appl. No. 13/930,533.
Non-Final Office action dated Dec. 19, 2013 for U.S. Appl. No. 13/646,947.
Nori, et al. Intracellular targeting of polymer-bound drugs for cancer chemotherapy. Advanced Drug Delivery Reviews 57 (2005): 609-636.
Notice of allowance dated Mar. 4, 2011 for U.S. Appl. No. 10/580,999.
Notice of allowance dated Mar. 8, 2012 for U.S. Appl. No. 12/935,110.
Notice of allowance dated Apr. 12, 2015 for U.S. Appl. No. 14/179,195.
Notice of allowance dated Jun. 19, 2013 for U.S. Appl. No. 13/097,364.
Notice of allowance dated Sep. 3, 2014 for U.S. Appl. No. 14/031,561.
Notice of allowance dated Apr. 14, 2014 for U.S. Appl. No. 13/513,145.
Notice of allowance dated Apr. 14, 2014 for U.S. Appl. No. 13/646,947.
Notice of allowance dated Sep. 14, 2012 for U.S. Appl. No. 12/935,110.
Notice of allowance dated Dec. 21, 2016 for U.S. Appl. No. 15/054,266.
Odian, G. (1991) Principles of Polymerization, Third Edition. John Wiley and Sons, Inc.
Office action dated Jan. 14, 2009 for U.S. Appl. No. 10/580,999.
Office action dated Feb. 5, 2014 for U.S. Appl. No. 14/031,561.
Office action dated Mar. 5, 2010 for U.S. Appl. No. 10/580,999.
Office action dated Apr. 24, 2012 for U.S. Appl. No. 13/097,364.
Office action dated Aug. 4, 2009 for U.S. Appl. No. 10/580,999.
Office action dated Sep. 20, 2012 for U.S. Appl. No. 13/097,364.
Office action dated Dec. 7, 2010 for U.S. Appl. No. 10/580,999.
Office Action from corresponding European Patent Application No. 10861515.4 dated Feb. 26, 2014, 6 pages.
Office Action from corresponding Japanese Patent Application No. 2013-547442 dated Oct. 29, 2014, with a Brief Report in English, 6 pages.
Owens, et al. Opsonization, biodistribution, and pharmacokinetics of polymeric nanoparticles. International Journal of Pharmaceutics 307 (2006): 93-102.
Patarroyo et al., Laminin Isoforms in Tumor Invasion, Angiogenesis, and Metastasis Seminars, Seminars in Cancer Biology, (Jume 2002), pp. 197-207, 12(3).
PCT/US2009/040252 International Preliminary Report on Patentability dated Oct. 21, 2010.
Peer, et al. Nanocarriers as an emerging platform for cancer therapy. Nat Nanotechnol. Dec. 2007;2(12):751-60.
Petajaniemi et al., Localization of Laminin a4-Chain in developing and Adult Human Tissues, The Journal of Hrstochemistry and Cytochemistry, (Aug. 2002), pp. 1113-1130, 50(8).
Pichon et al., Histidine-Rich Peptides and Polymers for Nucleic Acid Delivery, Advanced Drug Delivery Reviews, (2001), pp. 75-94, 53.
Qian et al., Targeted Drug Delivery via the Transferrin Receptor-mediated Endocytosis Pathway, Pharmacology Reviews. vol. 54, No. 4, (Dec. 2002), pp. 561-587.
Qin et al., The Transcription Factors Sp1, Sp3, and AP-2 are required for Constitutive Matrix Metalloproteinase-2 Gene Expression in Astroglioma Cells, Journal of Biological Chemistry, (Oct. 8, 1999), pp. 29130-29137.
Rameshwar, et al. Temozolomide Delivery to Tumor Cells by a Multifunctional Nano Vehicle Based on Ply (1-L-malic acid). Pharmaceutical Research, Kluwer Academic Publishers-Plenum Publishers, NL, 27.11 (2010): 2317-2329.

(56) References Cited

OTHER PUBLICATIONS

Saito et al., drug Delivery Strategy Utilizing Conjugation via Reversible Disulide Linkages: Role and Site of Cellular Reducing Activities, Advanced Drug Delivery Reviews, (2003), pp. 192-215, 55.
Samarsky et al., RNAi in Drug Development: Practical considerations, RNA Interference Technology, (2005), pp. 384-395.
Satchi, et al. Targeting angiogenesis with a conjugate of HPMA copolymer and TNP-470. Nature Medicine 10 (2004): 255-261.
Schnaible et al., identification of Fluorescein-5'-Isothiocynate-Modification Sites in Proteins by Electrospray—Ionization Mass Spectrosopy, Bioconjugates Chemistry, (1999), pp. 861-866, 10.
Segal, et al. Design and development of polymer conjugates as anti-angiogenic agents. Advanced Drug Delivery Reviews, 61 (2009): 1159-1176.
Sehgal, A., molecular Changes During the Genesis of Human Gliomas, Seminars in Surgical Oncology, (Jan.-Feb. 1998), pp. 3-12, 14(1).
Shi et al., Noninvasive Gene Targeting to the Brain, Proceedings of the National Academy of Sciences, (2000), pp. 7567-7572, 97.
Sixt et al., Endothelial Cell Laminin Isoforms, Laminins 8 and 10, Play Decisive Roles in T Cell Recruitement Across the Blood-Brain Barrier in Experimental Autoimmune Encephalomyelitis, Journal of Cell Biology, (May 28, 2001), pp. 933-947, 153(5).
Stummer, et al. Fluorescence-guided surgery with 5-aminolevulinic acid for resection of malignant glioma: a randomised controlled multicentre phase III trial. The Lancet Oncology, 7 (2006): 392-401.
Stupp et al., "Radiotherapy plus Concomitant and Adjuvant Temozolomide for Glioblastoma," N. Engl. J. Med. 352:987-996 (2005).
Summerton et al., Morpholino Antisense Oligomers: Design, Preparation and Properties, Antisense and Nucleic Acid Drug Development, (Jun. 1997), pp. 187-195, 7(3).
Taylor et al., Comparison of Efficacy of Antisense Oligomers Directed Toward TNF-a in Helper T and Macrophage Cell Lines, Cytokine, ((Sep. 1997), pp. 672-681, 9(9).
Thyboll et al., Deletion of the Laminin a4 Chain Leads to Impaired Microvessel Maturation, Molecular and Cellular Biology, (Feb. 2002), pp. 1194-1202, 22(4).

Trivedi, et al. Human methyl purine DNA glycosylase and DNA polymerase b expression collectively predict sensitivity to temozolomide. Mol Pharmacal. 74 (2008): 505-516.
Tsuji et al., Regulation of Melanoma Cell Migration and Invasion by Laminin-5 and a3(31 Integrin (VLA-3), Clinical and Experimental Metastasis, (2002), pp. 127-134, 19(2).
Vinogradov, et al. Mixed polymer micelles of amphiphilic and cationic copolymers for delivery of antisense oligonucleotides. Journal of Drug Targeting. 12 (2004): 517-526.
Voyta et al., Identification and Isolation of Endothelial Cells Based on Their Increased Uptake of Acetylated-Low Density Lipoprotein, Journal Of Cell Biology, (Dec. 1984), pp. 2034-2040, 99(6).
Waldeck, et al. TMZ-BioShuttle—A reformulated temozolomide. International Journal of Medical Sciences, Ivyspring International Publisher, Lake Haven, AU, 5.5 (2008): 273-284.
West record of CN1615855A, 2005, 2 pages.
Willner et al., (6-Maleimidocaproyl) Hydrazone of Doxorubicin—A New Derivative for the Preparation of Immunoconjugates of Doxorubicin, Boconjugate Chemistry, (193), pp. 521-527, 1993.
Wiseman, et al. Coexpression of the type 1 growth factor receptor family members HER-1, HER-2, and HER-3 has a synergistic negative prognostic effect on breast carcinoma survival. Cancer, 103.9 (2005): 1770-1777.
Written opinion dated Jun. 5, 2006 for PCT/US2004/040660.
Yu, et al. (2009) Targeted Delivery Systems for Oligonucleotide Therapeutics. The AAPS Journal, v.11(1):195-203.
Zagzag et al., Angiogenesis in the Central Nervous System: A role for Vascular Endothelial Growth FactorNascular Permeability Factor and Tenascin -C. Common Molecular Effectors in Cerebral Neoplastic and Non-Neoplastic "Angiogenic Diseases," Histol Histopathol, 17: 301-321, 2002.
Zhang et al., Antisense Gene Therapy of Brain Cancer with Artificial Virus Gene Delivery System, Molecular Therpay, vol. 6, No. 1 (Jul. 2002), pp. 67-72.
Zhao, et al. Synthesis and antitumour activities of 3-substituted 4-oxo-3 H-imidazo [5, 1-d][1,2,3,5] tetrazine-8- parboxylic acids and their derivatives. Chinese Journal of Medicinal Chemistry 11 (2001): 263-269.

DRUG DELIVERY OF TEMOZOLOMIDE FOR SYSTEMIC BASED TREATMENT OF CANCER

CROSS REFERENCE TO RELATED APPLICATIONS

This application is a continuation of U.S. patent application Ser. No. 15/054,266, filed Feb. 26, 2016, which is a continuation of U.S. patent application Ser. No. 14/179,195, filed Feb. 12, 2014, which is a continuation of U.S. patent application Ser. No. 13/513,145, filed Aug. 8, 2012, which is a 35 U.S.C. §371 national phase application of International Application No. PCT/US2010/059919, filed Dec. 10, 2010, which claims priority to U.S. Provisional Patent Application No. 61/285,495, filed Dec. 10, 2009; each incorporated by reference herein as if fully set forth.

STATEMENT REGARDING FEDERALLY SPONSORED RESEARCH OR DEVELOPMENT

This invention was made with government support under Grant No. CA123495 awarded by National Institutes of Health. The government has certain rights in the invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Malignant gliomas are the most common (60-70%) of all CNS/brain tumors. Annually there are approximately 5 cases of malignant gliomas per 100,000 people and over 14,000 new cases are diagnosed each year in the United States (1, 2). Surgery remains the standard therapy for primary brain tumors. Although surgery may be combined with radiation therapy and/or followed with chemotherapy to destroy remaining cancer cells, patients still have a poor survival advantage (3-5). In recent years, the prodrug Temozolomide (TMZ, TEMODAR), for example, which undergoes spontaneous conversion to the active alkylating agent, has emerged as a potent chemotherapeutic agent (6). In combination with radiotherapy, it has been shown to substantially increase median survival compared with radiotherapy alone (7). However, as with many potential chemotherapeutic agents, TMZ has considerable toxicity, which prevents therapeutic dosage increase. Moreover, another limiting factor of TMZ treatment is tumor resistance to the drug (8-10).

Thus, there is a need in the art for novel drug delivery systems that have tumor targeting, increased solubility, enhanced accumulation in solid tumors, decreased general toxicity, increased maximum tolerated doses, circumvention of multidrug resistance and enhanced apoptosis induction.

SUMMARY OF THE INVENTION

Various embodiments include a drug delivery system comprising a polymalic acid platform conjugated to a pro-drug, and one or more targeting antibodies, a trileucine (LLL) moiety, and/or a polyethylene glycol (PEG) moiety.

In another embodiment, the pro-drug comprises a therapeutically effective amount of a compound of the formula:

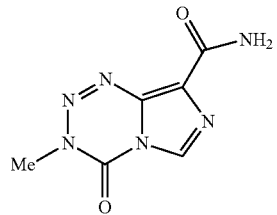 [SMILES: Cn1nnc2c(C(N)=O)ncn2c1=O]

(Formula 1), or a pharmaceutical equivalent, analog, derivative and/or salt thereof. In another embodiment, the one or more targeting antibodies is a monoclonal antibody to transferrin receptor (TfR). In another embodiment, the polymalic acid platform comprises a compound of the formula:

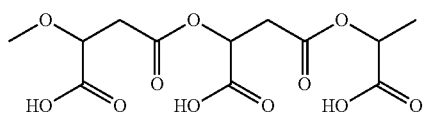 [SMILES: COC(CC(=O)OC(CC(=O)OC(C)C(=O)O)C(=O)O)C(=O)O]

(Formula 2), or a pharmaceutical equivalent, analog, derivative and/or salt thereof. In another embodiment, the one or more targeting antibodies is a anti-TfR humanized antibody. In another embodiment, the anti-TfR humanized antibody is used for active transport to a tumor. In another embodiment, one or more targeting antibodies is an anti-TfR mouse monoclonal antibody and/or an anti-TfR human monoclonal antibody.

Other embodiments include a pharmaceutical composition, comprising a therapeutically effective amount of a multifunctional nanoconjugate of temozolmide (TMZ), and a pharmaceutically acceptable carrier. In another embodiment, the multifunctional nanoconjugate of TMZ is a compound of the formula:

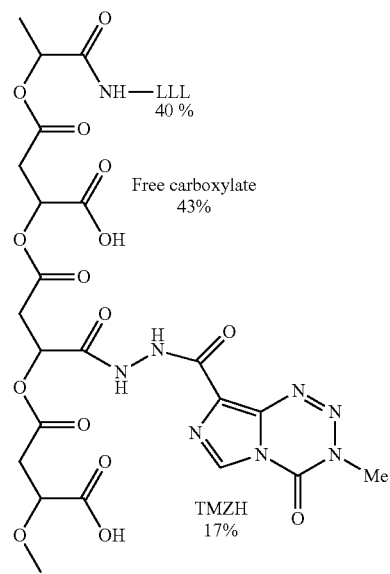

(Formula 3), or a pharmaceutical equivalent, analog, derivative and/or salt thereof. In another embodiment, the multifunctional nanoconjugate of TMZ is a compound of the formula:

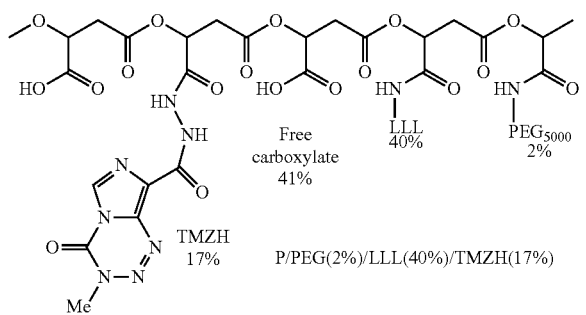

(Formula 4), or a pharmaceutical equivalent, analog, derivative and/or salt thereof.

Other embodiments include a method of treating a disease and/or condition in an individual, comprising administering a therapeutically effective dosage of a drug delivery system comprising a polymalic acid platform conjugated to a pro-drug, and one or more targeting antibodies, a trileucine (LLL) moiety, and/or a polyethylene glycol (PEG) moiety to the individual, and treating the individual. In another embodiment, the pro-drug comprises a therapeutically effective amount of a compound of the formula:

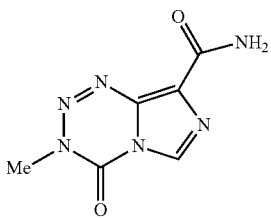 [SMILES: Cn1nnc2c(C(N)=O)ncn2c1=O]

(Formula 1), or a pharmaceutical equivalent, analog, derivative and/or salt thereof. In another embodiment, the therapeutically effective amount of the compound of the formula:

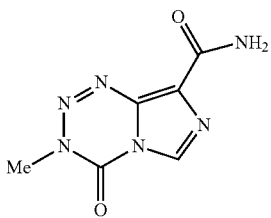 [SMILES: Cn1nnc2c(C(N)=O)ncn2c1=O]

(Formula 1), or a pharmaceutical equivalent, analog, derivative and/or salt thereof, is between 1 mg/kg and 10 mg/kg concentration. In another embodiment, the targeting antibody is a monoclonal antibody to transferrin receptor (TfR). In another embodiment, the polymalic acid platform comprises a compound of the formula:

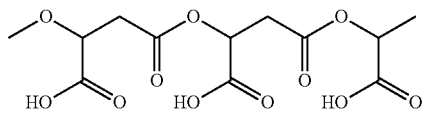 [SMILES: COC(CC(=O)OC(CC(=O)OC(C)C(=O)O)C(=O)O)C(=O)O]

(Formula 2), or a pharmaceutical equivalent, analog, derivative and/or salt thereof. In another embodiment, the drug delivery system comprises a compound of the formula:

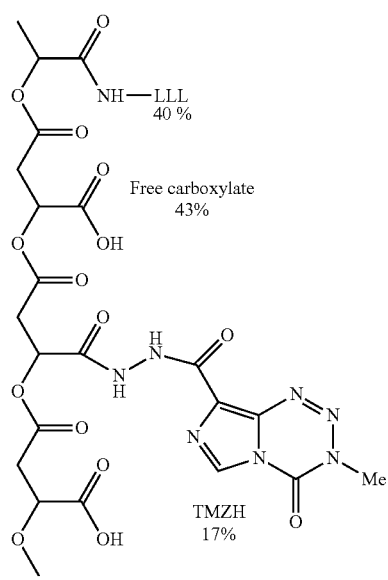

(Formula 3), or a pharmaceutical equivalent, analog, derivative and/or salt thereof. In another embodiment, the drug delivery system comprises a compound of the formula:

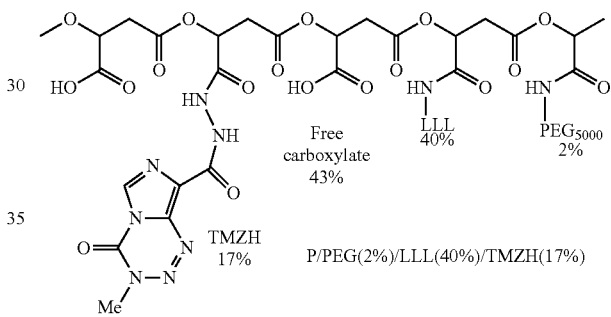

(Formula 4), or a pharmaceutical equivalent, analog, derivative and/or salt thereof. In another embodiment, the drug delivery system is administered to the individual intravenously. In another embodiment, the drug delivery system is administered to the individual at a concentration of about 4 mg/kg. In another embodiment, the drug delivery system is administered to the individual by direct injection and/or orally. In another embodiment, the drug delivery system is administered to the individual at a concentration of 75 mg/m$^2$. In another embodiment, the individual is a human. In another embodiment, the individual is a mouse and/or rat. In another embodiment, the drug delivery system comprises an anti-TfR mouse monoclonal antibody and/or an anti-TfR human monoclonal antibody. In another embodiment, the drug delivery system comprises an anti-TfR humanized antibody.

Various embodiments include a method of preparing a drug delivery system, comprising:
conjugating a compound of the formula:

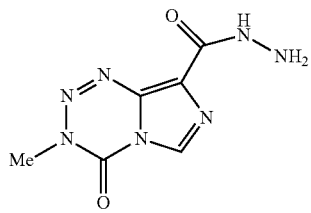

(Formula 5), or a pharmaceutical equivalent, analog, derivative and/or salt thereof, to an ionic polymalic acid. In another embodiment, the ionic polymalic acid comprises one or more targeting antibodies, a trileucine (LLL) moiety, and/or a polyethylene glycol (PEG) moiety. In another embodiment, the ionic polymalic acid comprises an anti-TfR humanized antibody for transporting to a tumor.

Other features and advantages of the invention will become apparent from the following detailed description, taken in conjunction with the accompanying drawings, which illustrate, by way of example, various embodiments of the invention.

DESCRIPTION OF THE INVENTION

Figure 1:
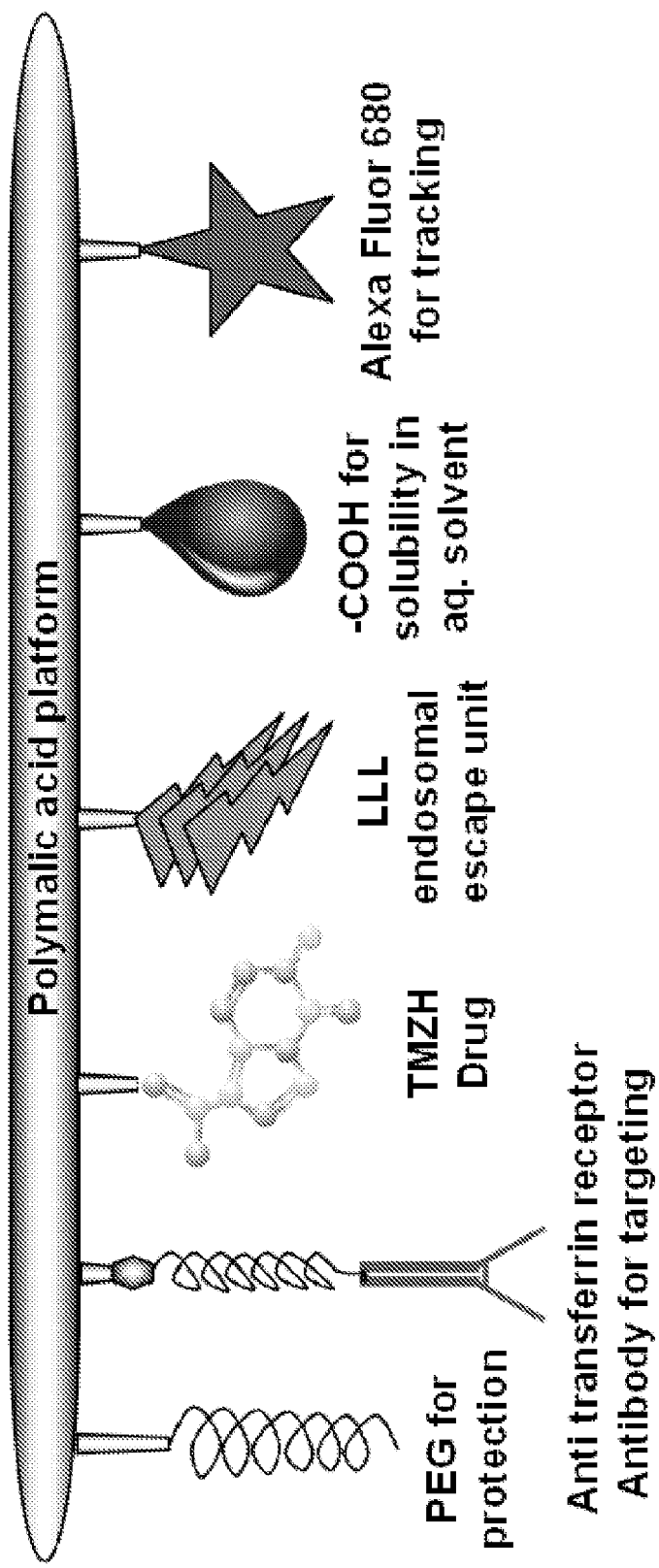
FIG. 1 depicts, in accordance with an embodiment herein, schematic presentation of the drug delivery system.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3$^{rd}$ ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, the term "TMZ" also refers to temozolomide, and is a compound of the formula:

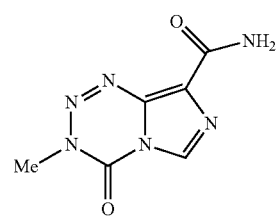 [SMILES: Cn1nnc2c(C(N)=O)ncn2c1=O]

(Formula 1), or a pharmaceutical equivalent, analog, derivative and/or salt thereof.

As used herein, the term "TMZH" also refers to temozolomide hydrazide, and is a compound of the formula:

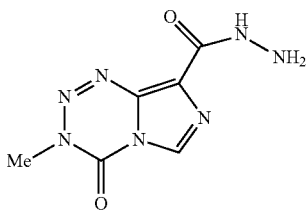 [SMILES: Cn1nnc2c(C(=O)NN)ncn2c1=O]

(Formula 5), or a pharmaceutical equivalent, analog, derivative and/or salt thereof.

As used herein, the term "PMLA" is an abbreviation for poly(β-L-malic acid), and is a compound of the formula:

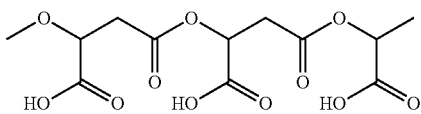 [SMILES: COC(CC(=O)OC(CC(=O)OC(C)C(=O)O)C(=O)O)C(=O)O]

(Formula 2), or a pharmaceutical equivalent, analog, derivative and/or salt thereof.

As used herein, the term "HuTfR mAb" means anti-human transferrin receptor monoclonal antibody.

As used herein, the term "LOEt" means L-leucine ethyl ester.

As used herein, the term "LLL" is an abbreviation of L-Leu-(L-Leu)-(L-Leu).

As used herein, the term "Alex680" means the fluorescent dye ALEXA FLUOR 680 C2 maleimide.

As used herein, the term "PMLA-LLL" includes PMLA containing LLL, which is conjugated by amide bond involving the N-terminal —$NH_2$.

As used herein, the term "PMLA-LLL40%" includes PMLA containing 40% of pendant carboxylates (100%) conjugated by amide bond involving the N-terminal —$NH_2$ of oligopeptide trileucine LLL.

As used herein, the term "Polycefin" is a general name for therapeutic nanoconjugates based on polymalic acid for drug delivery. It may contain multifunctional components, such as a drug, a targeting moiety, and an endosome escaping unit.

As disclosed herein, temozolomide (TMZ) is a pro-drug releasing a DNA alkylating agent that may treat glial tumors when combined with radiation. TMZ is toxic and therapeutic dosages are limited by severe side effects. Targeted delivery is thus needed to improve efficiency and reduce non-tumor tissue toxicity. The inventors synthesized multifunctional targetable nanoconjugates of TMZ hydrazide using a poly(β-L-malic acid) platform, which contained a targeting monoclonal antibody to transferrin receptor (TfR), trileucine (LLL) for pH-dependent endosomal membrane disruption, and PEG for protection.

In one embodiment, the present invention provides a composition comprising a multifunctional nanoconjugate of temozolomide (TMZ), or a pharmaceutical equivalent, analog, derivative, or salt thereof. In another embodiment, the multifunctional nanoconjugate of TMZ, or a pharmaceutical equivalent, analog, derivative, or salt thereof, comprises TMZ conjugated to an ionic polymalic acid. In another embodiment, the TMZ, or pharmaceutical equivalent, analog, derivative, or salt thereof comprises TMZ hydrazide. In another embodiment, the ionic polymalic acid comprises poly(β-L-malic acid). In another embodiment, the poly(β-L-malic acid) contains a targeting moiety, a pH-dependent endosome membrane disruption moiety, and/or a PEG moiety. In another embodiment, the targeting moiety comprises a targeting monoclonal antibody to transferrin receptor. In another embodiment, the endosome membrane disruption moiety comprises trileucine (LLL) and/or L-leucine ethyl ester (LoEt).

As further disclosed herein, the water-soluble TMZ nanoconjugates had hydrodynamic diameters in the range of 6.5 to 14.8 nm and ζ potentials in the range of −6.3 to −17.7 mV. 50% degradation in human plasma was observed in 40 h at 37° C. TMZ conjugated with polymer had a half-life of 5-7 h, compared with 1.8 h for free TMZ. The strongest reduction of human brain and breast cancer cell viability was obtained by versions of TMZ nanoconjugates containing LLL and anti-TfR antibody. TMZ-resistant cancer cell lines were sensitive to TMZ nanoconjugate treatment. TMZ-polymer nanoconjugates entered the tumor cells by receptor-mediated endocytosis, effectively reduced cancer cell viability, and can be used for targeted tumor treatment.

In one embodiment, the present invention provides a method of treating a cancer by administering a therapeutically effective dosage of a composition comprising a multifunctional nanoconjugate of temozolomide (TMZ), or a pharmaceutical equivalent, analog, derivative, or salt thereof, to an individual. In another embodiment, the multifunctional nanoconjugate of temozolomide (TMZ), or a pharmaceutical equivalent, analog, derivative, or salt thereof, is administered to the individual systemically. In another embodiment, the multifunctional nanoconjugate of temozolomide (TMZ), or a pharmaceutical equivalent, analog, derivative, or salt thereof, is administered to the individual systemically via intravenous administration. In another embodiment, the multifunctional nanoconjugate of temozolomide (TMZ), or a pharmaceutical equivalent, analog, derivative, or salt thereof, is administered to the individual orally and/or via direct injection. In another embodiment, the cancer is brain cancer. In another embodiment, side effects to the individual are minimized due to less free diffusion of the TMZ, wherein the TMZ is conjugated to a polycefin platform. In another embodiment, side effects to the individual are minimized to the individual due to specific tumor treatment and targeting resulting a homing device moiety of the multifunctional nanoconjugate of TMZ.

In conjunction with various embodiments described herein, the inventors have successfully conjugated TMZ via the hydrazide bond to the highly negatively charged PMLA that renders the prodrug no longer diffusible through membranes. This allows a highly more potent and effective delivery of TMZ (or other drugs). Unlike the conjugated TMZ form, the more traditional orally applied TMZ for treating human gliomas has the potency to be distributed all over the entire organism. After penetration of the lipophilic prodrug through membranes into the cytoplasm of recipient cells it will be activated by the hydrolytic mechanism described herein. The active drug is then ready to methylate proteins and especially DNA, guanine at N7 position, followed by methylation of adenine at the O3 position and of guanine at the O6 position (33). Failure of repair will drive these cells into apoptosis. Hydrolytic activation of the prodrug at sites other than the cytoplasm is inefficient due to the fact that the cationic methyl diazonium like any other charged molecule cannot passively penetrate membranes. However, in contrast, by conjugating TMZ and rendering the prodrug no longer diffusible through the membranes, the active methyl diazonium cation can only be generated from the nanodrug. Free passive diffusion of the PMLA conjugate into recipient cells is highly unlikely because of its high negative charge, and generation of active drug outside the cytoplasm would not be effective due to its own intrinsic charge. Therefore, the nanodrug can only give rise to nucleic acid methylation if it is internalized into the cytoplasm of recipient cells.

As further disclosed herein, a multifunctional nanoconjugate, or a pharmaceutical equivalent, analog, derivative, or salt thereof, was synthesized with PMLA as the platform and prodrug TMZ in its hydrazide form, $H_2N$-Leu-Leu-LeuOH (LLL) or $NH_2$-LeuOEt (LOEt) for disruption of endosomal membrane, antibodies for targeting, and PEG against resorption and enzyme degradation.

In one embodiment, the present invention provides a method of preparing a multifunctional nanoconjugate of temozolomide (TMZ), or a pharmaceutical equivalent, analog, derivative, or salt thereof by conjugating TMZ in its hydrazide form to a polycefin platform. In another embodiment, the multifunctional nanoconjugate of TMZ is prepared by the following steps, or a combination thereof: (1) chemical activation of the PMLA pendant carboxyl groups forming the NHS-ester and subsequently the nucleophilic replacement by forming stable amide bonds; (2) conjugation of antibodies via thioether bond formation, where because of the PMLA chain length inhomogeneity, an excess of mAb is chosen in order to increase the likelihood that at least one molecule was conjugated with each polymer chain; (3) conjugation with LLL, where because the amount of 40% of carboxyl groups conjugated with LLL for most efficient membrane disruption activity limits the amount of TMZH conjugation to 17%, in order to increase the amount of TMZH loading, (4) carboxyl activation is repeated after conjugation with LLL, (5) before conjugation with TMZH.

The present invention is also directed to a kit for materials for preparing a multifunctional nanoconjugate of temozolomide (TMZ), as well as the administration of the multifunctional nanoconjugate of TMZ to the individual, and may include a polymalic acid platform, PEG for protection, antibodies for targeting, TMZ molecules in hydrazide form, COOH for solubility in aqueous solvent, and tracking molecules such as the fluorescent dye ALEXA FLUOR 680, and combinations thereof. The kit is an assemblage of materials or components, including at least one of the inventive compositions.

The exact nature of the components configured in the inventive kit depends on its intended purpose. For example, some embodiments are configured for the purpose of treating brain cancer or drug delivery in mammalian subjects, such as, but not limited to, human subjects, farm animals, domestic animals, and laboratory animals.

Instructions for use may be included in the kit. "Instructions for use" typically include a tangible expression describing the technique to be employed in using the components of the kit to effect a desired outcome, such as to prepare a multifunctional nanoconjugate of TMZ and to deliver a therapeutically effective dosage of TMZ to an individual. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in preparing a nanoconjugate. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing a solution of multifunctional nanoconjugate of TMZ or components thereof. The packaging material generally has an external label which indicates the contents and/or purpose of the kit and/or its components.

In various embodiments, the present invention provides pharmaceutical compositions including a pharmaceutically acceptable excipient along with a therapeutically effective amount of Polycefin-LLL. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to an intravenous injection, aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective delivery of a multifunctional nanoconjugate of TMZ, or a pharmaceutical equivalent, analog, derivative, or salt thereof, can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

As described herein, various embodiments of the invention include the therapeutically effective delivery of a multifunctional nanoconjugate of TMZ, or a pharmaceutical equivalent, analog, derivative, or salt thereof, to an individual in treatment of brain cancer. As readily apparent to one of skill in the art, the invention may be applied to any number of targets where it would be beneficial to deliver a drug or molecule to an individual while decreasing side effects due to less free diffusion and/or targeted delivery. Similarly, any number of conditions and/or diseases may be beneficially treated and the invention is in no way limited to treatment of brain cancer and/or tumor suppression. For example, various embodiments described herein may include the treatment of HIV and/or AIDS, and any other number of conditions where it is advantageous to deliver a therapeutically effective dosage of a drug. Finally, as would be readily apparent to one of skill in the art, various molecules and/or drugs may also be delivered, including the delivery of proteins, and the various embodiments described herein are in no way limited to delivery of TMZ, or its pharmaceutical equivalent, analog, derivative, or salt thereof.

Various embodiments of the invention may also be practiced in conjunction with an overall treatment regimen. For example, as described herein, various embodiments include the delivery of TMZ by way of disruption of the endosome. As readily apparent to one of skill in the art, additional drugs or substances that were previously inactive in the endosome will then become active upon the disruption of the endosome. Thus, various embodiments of the invention may include additional drugs or substances administered to the subject being treated and the invention is not only limited to drugs and/or molecules covalently linked to the scaffold as described herein. Similarly, as readily apparent to one of skill in the art, various embodiments of the invention may be used in conjunction with or in combination with additional therapeutics.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

General

Temozolomide (TMZ) is a pro-drug releasing a DNA alkylating agent that may treat glial tumors when combined with radiation. TMZ is toxic and therapeutic dosages are limited by severe side effects. Targeted delivery is thus needed to improve efficiency and reduce non-tumor tissue toxicity. The inventors synthesized multifunctional targetable nanoconjugates of TMZ hydrazide using a poly(β-L-malic acid) platform, which contained a targeting monoclonal antibody to transferrin receptor (TfR), trileucine (LLL) for pH-dependent endosomal membrane disruption, and PEG for protection.

As further disclosed herein, the water-soluble TMZ nanoconjugates had hydrodynamic diameters in the range of 6.5 to 14.8 nm and ζ potentials in the range of −6.3 to −17.7 mV. 50% degradation in human plasma was observed in 40 h at 37° C. TMZ conjugated with polymer had a half-life of 5-7 h, compared with 1.8 h for free TMZ. The strongest reduction of human brain and breast cancer cell viability was obtained by versions of TMZ nanoconjugates containing LLL and anti-TfR antibody. TMZ-resistant cancer cell lines were sensitive to TMZ nanoconjugate treatment. TMZ-polymer nanoconjugates entered the tumor cells by receptor-mediated endocytosis, effectively reduced cancer cell viability, and can be used for targeted tumor treatment.

Example 2

Reagents Used

TMZ was purchased from AK Scientific, Inc. (Mountain View, Calif., USA). TMZ hydrazide (TMZH) was synthesized from TMZ as described (25). Mouse anti-human TfR mAb RVS10 was purchased from Southern Biotech (Birmingham, Ala., USA). PMLA (100 kDa; polydispersity 1.3; hydrodynamic diameter 6.6 nm; ζ potential −22.5 mV, pH 7.5 at 25° C.) was obtained from culture broth of *Physarum polycephalum* as described (26). mPEG$_{5000}$-amine and maleimide-PEG$_{3400}$-maleimide were obtained from Laysan Bio, Inc. (Arab, Ala., USA). NH$_2$-Leu-OEt (LOEt) and NH$_2$-Leu-Leu-Leu-OH (LLL) were purchased from Bachem Americas, Inc. (Torrance, Calif., USA). Egg yolk and phosphatidylcholine from Fluka (Buchs, Switzerland). 3-(2-Pyridyldithio)-propionate (PDP) was synthesized as described (27). The fluorescent dye ALEXA FLUOR 680 C2 maleimide (Alex680) was from Invitrogen Corporation (Carlsbad, Calif., USA). Unless otherwise indicated, all chemicals and solvents of highest purity were purchased from Sigma-Aldrich (St. Louis, Mo.) USA.

Example 3

Analytical Methods for Chemical Synthesis

The conjugation reaction of PMLA with PEG, TMZH, LLL and LOEt was followed by thin layer chromatography (TLC) on precoated silica gel 60 F254 aluminum sheets (Merck, Darmstadt, Germany) and visualization of spots by UV light and/or by ninhydrin staining. The concentration of free or conjugated TMZH was monitored by reading A$_{328}$ and using known amounts of TMZ or TMZH standards. Size exclusion chromatography was performed on LACHROM ELITE, an analytical High Performance Liquid Chromatograph (HPLC) system with Diode Array Detector L 2455 (Hitachi, Pleasanton, Calif., USA), and M$_w$ was measured using BioSep-SEC-S 3000 (300×7.80 mm) (Phenomenex, Torrance, Calif., USA) with 50 mM sodium phosphate buffer pH 6.8 and polystyrene sulfonates as molecular weight standards. Thiol residues attached to PMLA were assayed by the method of Ellman. Enzyme-linked immunosorbent assay (ELISA) was used to determine the functional activity of conjugated antibody using a Protein Detector ELISA Kit (KPL, Inc., Gaithersburg, Mass., USA). Human TfR ectodomain used as antigen was obtained from Protein Expression Center, California Institute of Technology, Pasadena, USA.

Example 4

Syntheses of Nanoconjugates

Figure 10:
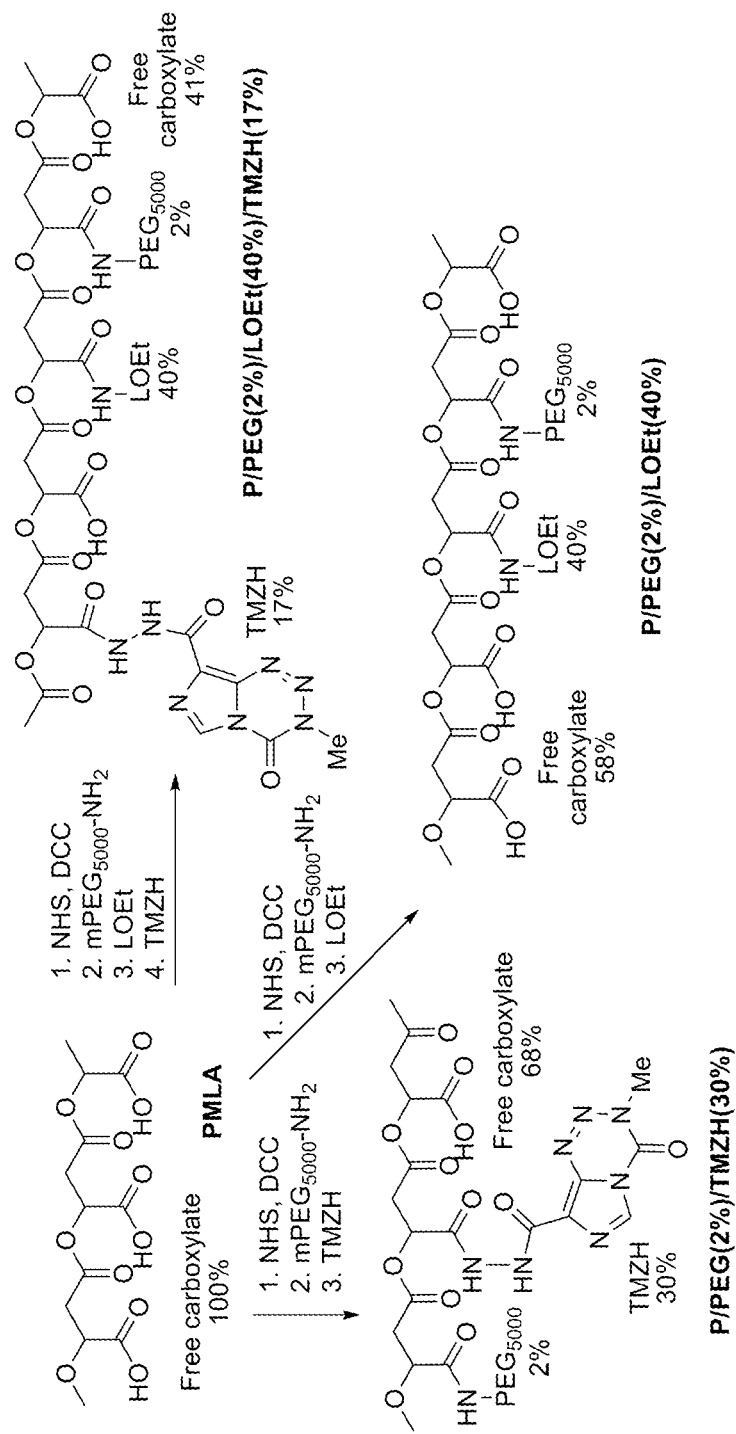
FIG. 10 depicts, in accordance with an embodiment herein, synthetic strategy for LOEt conjugates containing TMZH.
Figure 11:
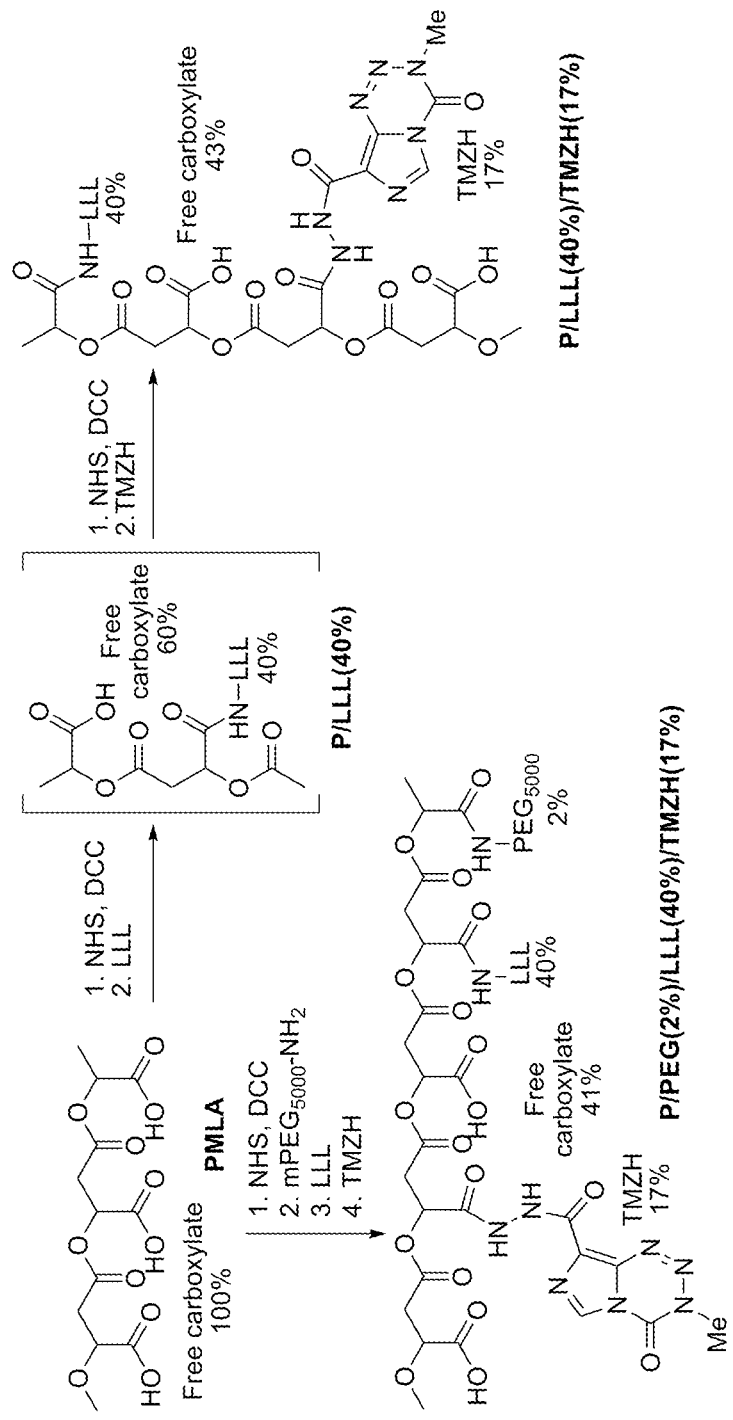
FIG. 11 depicts, in accordance with an embodiment herein, synthetic strategy for LLL conjugates containing TMZH.

A variety of conjugates were synthesized in order to examine the effect of each conjugated functional group on membrane disruption and cell viability. Two membrane disrupting units were examined for their usefulness in endosome escape: LOEt and LLL. The synthetic strategies for the nanoconjugates containing the LOEt endosomal escape unit are summarized in FIG. 10 and for those containing LLL endosomal escape unit, in FIG. 11. Conjugates containing different amounts of TMZH were synthesized by analogous methods.

Example 5

Conjugate P/PEG(2%)/TMZH(30%)

N-Hydroxysuccinimide (NHS) (1 mmol) and N,N'-dicyclohexylcarbodiimide DCC (1 mmol) dissolved in 2 ml of DMF were added consecutively to the solution of 116 mg of PMLA (1 mmol with regard to malyl units) dissolved in 1 ml of anhydrous acetone under vigorous stirring at room temperature (RT). The reaction mixture became turbid almost immediately upon addition of the NHS/DCC mixture indicating the formation of dicyclohexylurea. After stirring at RT for 3 h to complete the activation of carboxyl groups, 0.02 mmol of mPEG$_{5000}$-NH$_2$ (in 0.5 ml of DMF, 2 Mol-% with regard to malyl units) was added followed by 0.02 mmol of triethylamine (TEA). After the reaction was completed according to TLC/ninhydrin test, the reaction mixture was filtered and most of the solvent was removed by rotary evaporation. Next, 0.3 mmol of TMZH (15 mg/ml in DMF, 30 Mol-% with regard to malyl units) was added drop-wise at RT under stirring followed by 0.3 mmol of TEA. The reaction was complete within 2 h according to TLC (Rf=0.4 for TMZH; Rf=0 for the polymer conjugate; chloroform:methanol 9:1; visualization under UV and by ninhydrin). Addition of 5-6 ml 100 mM sodium phosphate buffer containing 150 mM NaCl (pH 6.0) to the reaction mixture was followed by 30 min stirring at RT. After centrifugation at 1500×g for 10 min the clear supernatant was passed over a SEPHADEX column (PD-10, GE Healthcare, Piscataway, N.J., USA) pre-equilibrated with deionized (DI) water. The product containing fractions were collected and conjugate P/PEG(2%)/TMZH(30%) was obtained after freeze drying.

Example 6

Conjugate P/PEG(2%)/LOEt(40%)/TMZH(17%)

PMLA activation and conjugation of PEG followed the method described for conjugate P/PEG(2%)/TMZH(30%). A solution of LOEt hydrochloride (200 mM in DMF, 40 Mol-% with regard to malyl units) was added drop-wise at RT under stirring followed by addition of 0.4 mmol of TEA. The reaction was complete after 2 h according to TLC (Rf=0 for the polymer conjugate, Rf=0.67 for LOEt; n-butanol: acetic acid:water 4:2:2) and visualization of spots by ninhydrin. Next, 0.17 mmol of TMZH (15 mg/ml in DMF, 17 Mol-% with regard to malyl units) was added drop-wise under stirring at RT followed by 0.17 mmol of TEA. After reaction completion in 2 h as judged by TLC (Rf=0.4 for TMZH; Rf=0 for the polymer conjugate; chloroform:methanol 9:1), UV and ninhydrin test, conjugate was dissolved in phosphate buffer, isolated as described for P/PEG(2%)/TMZH(30%), and freeze dried. To isolate the intermediate product P/PEG(2%)LOEt(40%), the same method for isolation was used and the product was obtained after freeze drying.

Example 7

Synthesis of Conjugate P-LLL(40%)/TMZH(17%)

PMLA activated at carboxyl groups was prepared as described for conjugate P/PEG(2%)/TMZH(30%). A solution of LLL, 0.4 mmol, 50 mg/ml in DMF (40 Mol-% with regard to malyl units) and TFA (125 Mol-% with regard to LLL, to dissolve the tripeptide) was added at RT. TEA (0.4 mmol in DMF, 1:25 v/v) was then added slowly over 30 min.

After 2-3 h the reaction was complete by TLC (Rf=0 for polymer conjugate; Rf=0.6 for LLL; n-butanol:acetic acid: water 4:2:2) and by ninhydrin test. Conjugate P/LLL(40%) was dissolved in phosphate buffer and isolated as described for conjugate P/PEG(2%)/TMZH(30%). In order to maximize TMZH loading, a second round of carboxyl activation was performed: A solution of NHS (0.217 mmol) and of DCC (0.217 mmol) in 1 ml of DMF were added consecutively to the solution of 56 mg of P/LLL(40%) (0.217 mmol of free acid groups) dissolved in 1 ml of anhydrous DMF under vigorous stirring at RT. After stirring for 3 h at RT, 0.037 mmol of TMZH (15 mg/ml in DMF, 17 mol % with regard to malyl units) was added drop-wise at RT, followed by 0.037 mmol of TEA. The reaction mixture was stirred at RT for 3 h and the conjugate was isolated as described for P/PEG(2%)/TMZH(30%).

Example 8

Synthesis of
P/PEG(2%)/LLL(40%)/TMZH(17%)/MEA(3%)

This conjugate was used for the conjugation of antibody. The conjugate not containing 2-MEA was synthesized in the absence of this reagent. PMLA activated at carboxyl groups was prepared as described for conjugate P/PEG(2%)/TMZH (30%). A solution of LLL, 0.4 mmol, in DMF 50 mg/ml (40 Mol-% with regard to malyl units) and TFA (125 Mol-% with regard to LLL) was added drop-wise to dissolve the tripeptide at RT. TEA 0.4 mmol in DMF (1:25 v/v) was then added slowly over 30 min. The reaction was complete after 2-3 h by TLC (Rf=0 for polymer conjugate; Rf=0.6 for LLL; n-butanol:acetic acid:water 4:2:2) and by ninhydrin test. Next, TMZH (15 mg/ml in DMF, 17 Mol-% or optionally 30 Mol-% with regard to malyl units) was added drop-wise under stirring at RT followed by equivalent amount of TEA. After reaction completion in 2-3 h, as judged by TLC (Rf=0.4 for TMZH; Rf=0 for the polymer conjugate; chloroform:methanol 9:1), UV, and ninhydrin test, 0.05 mmol of 2-MEA in DMF (100 µl, 5 Mol-% with regard to malyl units) was added to the reaction mixture. After reaction completion in 30-40 mM (TLC and ninhydrin test), conjugate was dissolved in phosphate buffer and isolated as described for conjugate P/PEG(2%)/TMZH(30%).

Example 9

Conjugate
P/PEG(2%)/LLL(40%)/TMZH(17%)/HuTfR
mAb(0.25%)

A solution of Anti-human TfR mAb (HuTfR)/PEG$_{3500}$/maleimide (2 mg/ml) synthesized as described (28) and dissolved in 100 mM sodium phosphate buffer containing 150 mM NaCl (pH 6.0) was added dropwise at room temperature to a solution of P/PEG(2%)/LOEt(40%)/TMZH (17%)/MEA(3%) at 2 mg/ml in the same buffer. After stirring overnight at 4° C., remaining free —SH groups were blocked by excess PDP (50 mg/ml in DMF) by stirring for 30 mM at room temperature. The product was concentrated over a centrifuge membrane filter VIVASPIN 20, cutoff 30 kDa, 20 ml at 1500×g (Sartorius Stedim Biotech, Concord, Calif., USA), and the final volume was adjusted to 2 ml before purification over SEPHADEX G-75 pre equilibrated with buffer, sodium phosphate 100 mM, NaCl 150 mM, pH 6.8. Product containing fractions were isolated, combined and concentrated via membrane filtration. Similar methods were used to synthesize other antibody containing conjugates.

Example 10

Fluorescent Labeling of Conjugates

Alex680 dissolved in DMF at 1 mg/ml was added to the solution of desired conjugates (2 mg/ml) in 100 mM sodium phosphate buffer with 150 mM NaCl, pH 5.5. The reaction mixture was stirred at RT for 1 h and passed over SEPHADEX G-75 pre equilibrated with 100 mM sodium phosphate buffer, 150 mM NaCl, pH 6.8. The product was concentrated via membrane filtration. For the antibody containing conjugates, Alex680 labeling was performed before blocking of excess free thiol groups by PDP.

Example 11

Calculation of Molecular Weights of
Nanoconjugates

Molecular weights of nanoconjugates were calculated as shown for conjugate P/PEG(2%)/LLL(40%)/TMZH(17%) as an example: 100% malic acid residues (FW 116)=862 monomers of PMLA (Mw=100 kDa). Mw fraction of malic acid with free —COOH (FW116) is 41%=353.4×116 Da: 41.0 kDa. Fraction conjugated malic acid (FW 99) is 59%=508.6×99 Da: 50.3 kDa. Fraction mPEG$_{5000}$ (FW 5000) is 2%=17.2×5000 Da: 86.2 kDa. Fraction LLL (FW 357.5) is 40%=344.8×357.5 Da: 123.3 kDa. Fraction TMZH (FW 210.63) is 17%=146.5×210.63: 30.8 kDa. Total estimated average Mw of conjugate is 332 kDa.

Example 12

Hydrodynamic Diameter and Zeta Potential

Synthesized conjugates were characterized with respect to their size and ζ potential using a particle and molecular size analyzer ZETASIZER Nano ZS90 (Malvern Instruments, Malvern, UK). The size was calculated on the basis of noninvasive back-scattering (NIBS) measurements using the Stokes-Einstein equation, $d(H)=kT/3\pi\eta D$. d(H) is the hydrodynamic diameter, D translational diffusion coefficient, k Boltzmann's constant, T absolute temperature, and η viscosity. The diameter that is measured in DLS (Dynamic Light Scattering) refers to the particle diffusion within a fluid and is referred to as the hydrodynamic diameter corresponding to the diameter of a sphere that has the same translational diffusion coefficient as the particle. The ζ potential was calculated from the electrophoretic mobility based on the Helmholtz-Smoluchowski formula, using electrophoresis M3-PALS (29, 30). All calculations were carried out by the ZETASIZER 6.0 software. For the particle size measurements at 25° C., the solutions were prepared in PBS at a concentration of 2 mg/ml, filtered through a 0.2 µm pore membrane. For the measurement of the ζ potential, the concentration of the sample dissolved in water containing 10 mM NaCl was 2 mg/ml, and the voltage applied was 150 V. All the conjugate solutions were prepared immediately before analysis at 25° C. Data represent the mean±standard deviation obtained for three measurements.

Example 13

Liposome Leakage Assay

Fluorescent assay for calcein release from loaded phosphatidylcholine/cholesterol liposomes (31) purified over the SEPHADEX G-50 gel was used to determine leakage activity of synthesized polymer conjugates. To assess leakage at different pH values, nanoconjugates were serially diluted in 50 µl buffer containing appropriate mixtures of 137 mM HEPES, pH 7.4 and 137 mM citrate, pH 5.0. Triplicate samples were mixed with 50 µl liposome suspensions in 5 mM HEPES buffer, 150 mM NaCl, pH 7.4 (final lipid concentration 160 µM). After 1 h at RT, fluorescence was read by an ELISA reader at 485 nm excitation and 535 nm emission wavelengths. The detergent TRITON X-100, 0.25% (v/v), was used as a reference for 100% leakage.

Example 14

Conjugate Degradation Study

The degradation of nanoconjugates in human plasma was carried out at 37° C. with a polymer concentration of 1 mg/ml. The sample vials were sealed to avoid evaporation and stored at 37° C. in an incubator. For the isolation from the plasma, aliquots of 1 ml were extracted with 5 ml of chloroform/ethyl acetate (1:1 v/v). The copolyester contained in the organic phase was dried and re-dissolved in PBS buffer. Size reduction due to degradation was followed by measurement of the hydrodynamic diameter in a particle and molecular size analyzer ZETASIZER or of the molecular weight by SEC-HPLC. Sample preparation with the polymers of known Mw was used to verify that the isolation method had no effect on molecular weights. Degradation in PBS (pH 7.4) was followed at a concentration of 1 mg/ml for each copolymer. The change in size of the nanoconjugate either by SEC-HPLC or hydrodynamic diameter (a particle and molecular size analyzer ZETASIZER) was measured as a function of degradation time. Molecular weights $M_w(t)$ and hydrodynamic diameter (t) were plotted as a function of degradation time with reference of these properties at zero incubation time.

Example 15

Cell Viability

Primary glioma cell lines U87MG and T98G, and invasive breast carcinoma cell lines MDA-MB-231 and MDA-MB-468 were obtained from American Type Culture Collection (ATCC, Manassas, Va., USA) USA. U87MG and T98G cells were cultured in MEM supplemented with 10% fetal bovine serum, 1% MEM NEAA, 1 mM sodium pyruvate and 2 mM L-glutamine. For MDA-MB-231 and MDA-MB-468, Leibovitz's L-15 medium with 10% fetal bovine serum was used. Cells were seeded at $10^3$ per well (0.1 ml) in 96-well flat-bottomed plates and incubated overnight at 37° C. in humid atmosphere with 5% $CO_2$ (MDA-MB-231 and MDA-MB-468 were incubated without $CO_2$). After exposure to synthesized conjugates for 24 h, medium was replaced every 48 h. Cell viability was measured on day 5 for T98G and day 7 for the rest of the cell lines using the CELLTITER 96 Aqueous One Solution Cell Proliferation Assay kit (Cat. No. PR-G3580; Promega, Madison, Wis., USA). Yellow [3-(4,5-dimethylthiazol-2-yl)-5-(3-carboxymethoxyphenyl)-2-(4-sulfophenyl-)-2H-tetrazolium, inner salt] (MTS) is bioreduced by cells into formazan that is soluble in the tissue culture medium. The absorbance reading at 490 nm from the 96-well plates is directly proportional to the number of living cells (32). The viability of the untreated cells was taken as 100%. The results shown are the means±standard deviation of three independent measurements. Data were analyzed by statistical software GRAPHPAD PRISM 3.0.

Example 16

Confocal Microscopy $1\times10^5$ U87MG cells were seeded on Lab-Tek chamber slides (Thermo Fisher Scientific, Rochester, N.Y., USA) for 24 h. The cells were washed once with serum-free media and incubated with Alex680 fluorescently labeled conjugates in 500 µl serum-free media at 50 µg/ml for P/PEG(2%)/LLL (40%)TMZH(17%)/Alex680(1%) and at 100 µg/ml for P/PEG(2%)/LLL(40%)TMZH(17%)/HuTfR mAb(0.25%)/Alex680(1%). After 1 h incubation at 37° C. in humid atmosphere with 5% $CO_2$, the cells were washed three times with PBS and finally incubated in fresh media with serum for live confocal imaging in a TCS SP spectral scanner (Leica Microsystems, Mannheim, Germany) Image stacks of 246 by 246 µm in size and 7.5 µm in depth of live U87MG glioma cells were acquired with a HCX PL APO CS 63.0×1.20 lens. Live cells were placed on chamber slides maintaining 37° C. temperature, humidity and 5% $CO_2$ by a separate lens and chamber heating system. The spectral settings were optimized for Alex680, excitation 670 nm and emission 685-750 nm. The images were processed by ImageJ 1.410 software from NIH.

Example 17

Nanoconjugate Syntheses

The multi component drug delivery system schematically presented in FIG. 1 was synthesized with PMLA as the platform and prodrug TMZ in its hydrazide form, $H_2N$-Leu-Leu-LeuOH (LLL) or $NH_2$-LeuOEt (LOEt) for disruption of endosomal membrane, antibodies for targeting, and PEG against resorption and enzyme degradation. The first part of the conjugation included the chemical activation of the PMLA pendant carboxyl groups forming the NHS-ester and subsequently the nucleophilic replacement by forming stable amide bonds. Conjugation of antibodies via thioether bond formation followed in the second part. Because of the PMLA chain length inhomogeneity, an excess of mAb was chosen in order to increase the likelihood that at least one molecule was conjugated with each polymer chain. The amount of 40% of carboxyl groups conjugated with LLL for most efficient membrane disruption activity limited the amount of TMZH conjugation to 17%. In order to increase the amount of TMZH loading, carboxyl activation was repeated after conjugation with LLL before conjugation with TMZH. Obtained nanoconjugates of higher than 17% TMZH were, however, found insoluble in aqueous buffer. Care was taken to avoid neutral or alkaline conditions as well as elevated temperatures (>22° C.) in order to keep hydrolytic degradation of TMZ at a minimum. Freeze-dried intermediates and products could be stored at −20° C. for several months without measurable loss in chemical or physiological reactivity.

Example 18

Purity and Physicochemical Characterization

Figure 2:
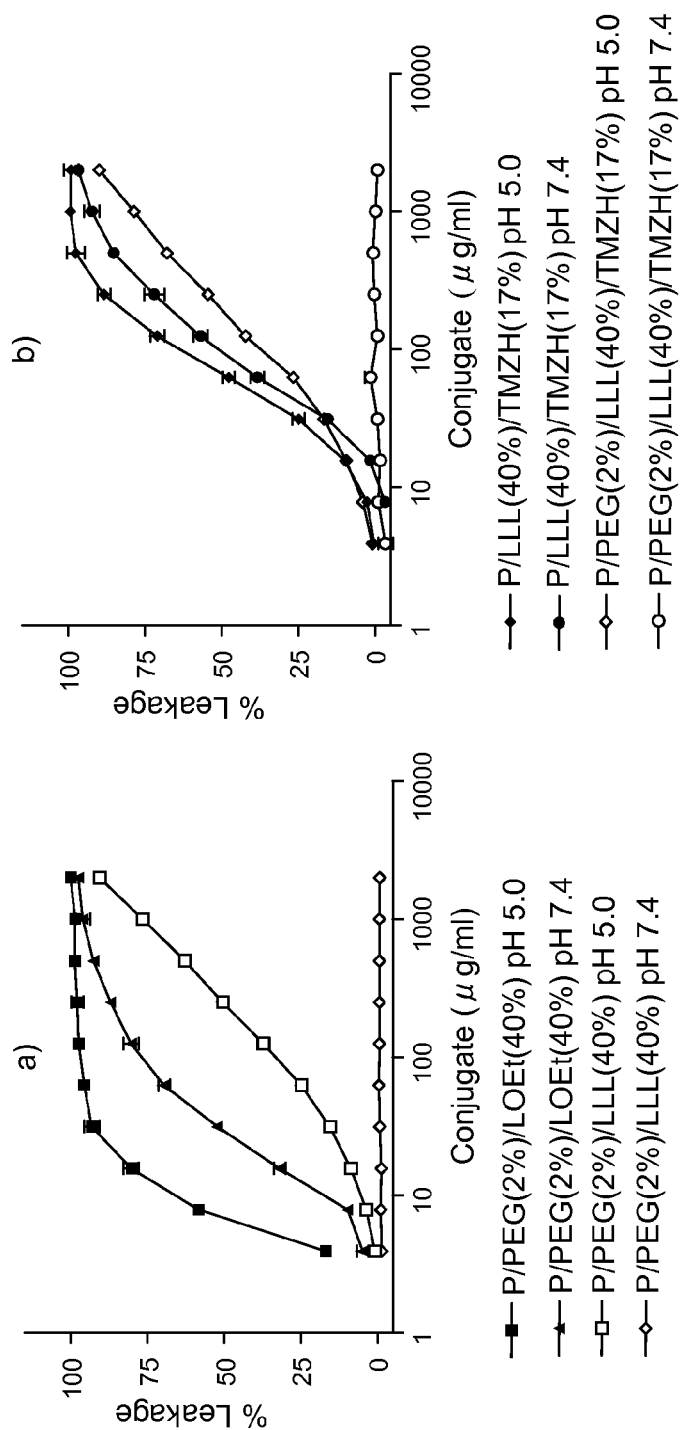
FIG. 2 depicts, in accordance with an embodiment herein, liposomal leakage assay: a) Liposome leakage of P/LOEt and P/LLL conjugates, b) Liposome leakage of P/LLL/TMZH and P/PEG/LLL/TMZH conjugates. Percentage refers to ratio of pendant —COOH conjugated (total PMLA pendant —COOH is 100%). % Leakage compared to complete leakage in the presence of the detergent TRITON X-100 0.25% (v/v).
Figure 6:
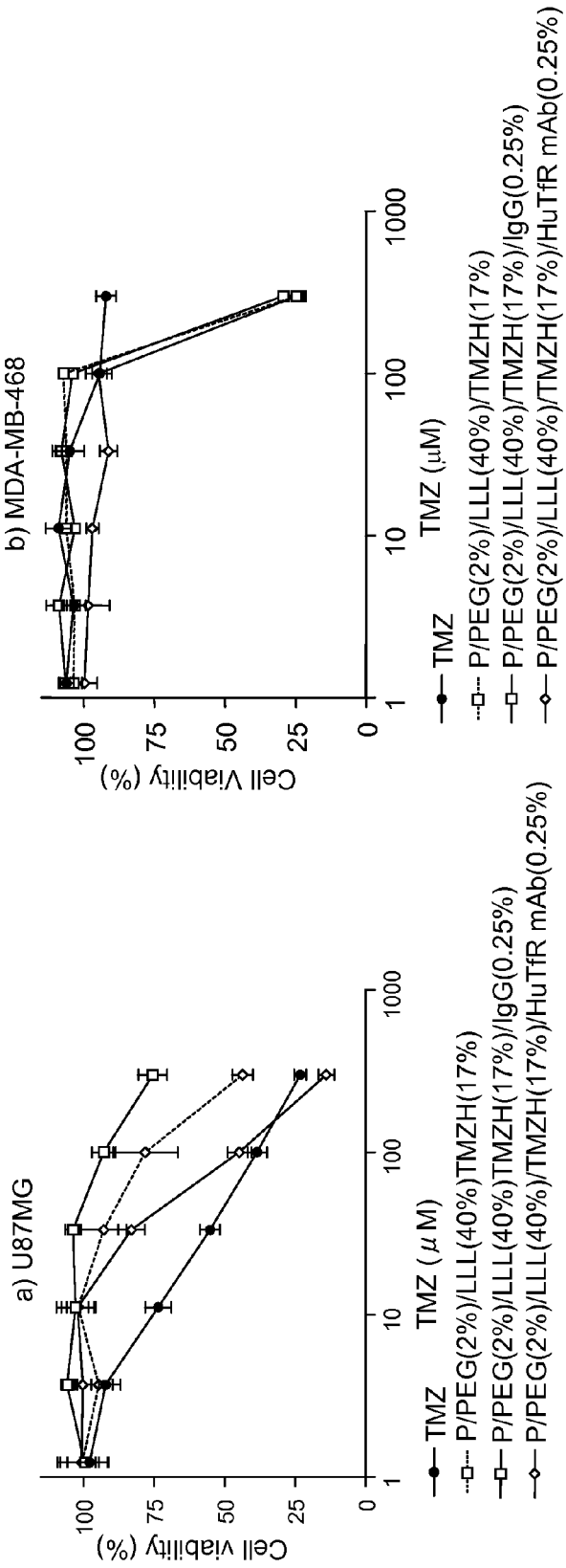
FIG. 6 depicts, in accordance with an embodiment herein, cell viability of LLL nanoconjugates with antibody: Effects on cell viability of TMZ, P/PEG(2%)/LLL(40%)/TMZH (17%), P/PEG(2%)/LLL(40%)/TMZH(17%)/IgG(0.25%), P/PEG(2%)/LLL(40%)/TMZH(17%)/HuTfR mAb(0.25%) on a) U87MG and b) MDA-MB 468 cells. Conjugation of HuTfR mAb increased the activity of drug on U87MG cell line, whereas no such effect was observed on MDA-MB-468.

Products were highly soluble in aqueous solution without forming precipitates as judged by SEC-HPLC and a particle and molecular size analyzer ZETASIZER. Preparations were tested for small molecular weight impurities by TLC and ninhydrin reaction. On this basis of SEC-HPLC results (using multiple wavelengths for scanning) and hydrodynamic diameter scanning, the investigated conjugates were pure, i.e. consisting of single compounds. The amount of TMZH in the conjugate preparations was validated by UV absorbance at 328 nm using known amounts of free TMZH as standards. By $^1$H NMR analysis using integration of methyl group signals of TMZH and of PMLA protons the TMZH contents were analyzed. TMZ contents by NMR and UV measurement were the same within 3% deviation measured for conjugate P/PEG(2%)/TMZH(30%). Conjugates had characteristic values of hydrodynamic diameters and zeta potentials (Table I). Free PMLA and P/LLL(40%)/TMZH(17%) had the smallest hydrodynamic diameter, whereas additionally conjugated $PEG_{5000}$ increased the diameter by about 2 nm and mAb, by about 8 nm. The value of $\zeta$ potential can be used to differentiate between PMLA, −22.9 mV, and nanoconjugates with neutral ligands like TMZH, LOEt, for example −7 mV for P/PEG(2%)/LOEt (40%)/TMZH(17%), and conjugates with charged ligands like LLL (instead of LOEt), for example −11.5 mV for P/PEG(2%)/LLL(40%)/TMZH(17%) (Table 1). Conjugates were also distinguished by other properties, e.g., by their capability for liposome leakage. As shown in FIG. 2, the conjugate P/PEG(2%)LLL(40%)/TMZH(17%) was pH-sensitive, whereas the conjugate P/LLL(40%)/TMZH(17%) was not. Another property was the effect on U87MG and MDA-MB-468 cell viability. It was more affected by the conjugate P/LLL(40%)/TMZH(17%) (FIG. 4) than by P/PEG(2%)LLL(40%)/TMZH(17%) (FIG. 6).

Example 19

Half-Life of Free and Conjugated TMZH

TMZ is a prodrug and undergoes spontaneous conversion to the active alkylating agent at neutral or alkaline pH. Half-lives were measured at physiological pH 7.4 in PBS and summarized in Table I. The decomposition of free and conjugated TMZH by hydrolytic ring opening (Chart 1) was a first order reaction for free TMZ or TMZH and conjugated TMZH (data not shown). For TMZ, the half-life was 1.80±0.1 h and for TMZH, 1.98±0.1 h. Half-life was significantly enhanced, about 3-4 times, after conjugation with the polymer. For example, TMZ had a half life of 7.34±0.2 h for conjugate P/LLL(40%)/TMZH(17%) and 7.10±0.2 h for P/PEG(2%)/TMZH(30%) (Table I). Similar data have been reported for TMZ conjugated with small carbon chains (6). No detectable decomposition was observed during 24 h at pH 5.0 at RT.

Example 20

Stability and Degradation Measured by Size

Figure 3:
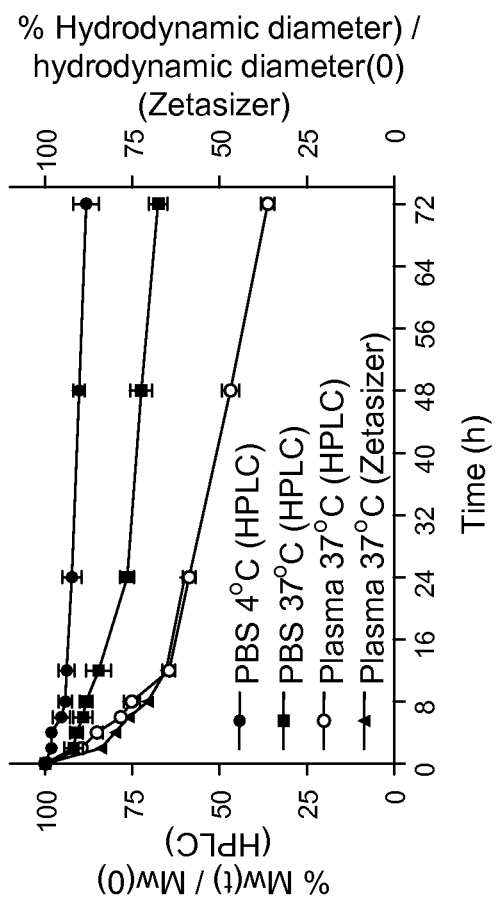
FIG. 3 depicts, in accordance with an embodiment herein, nanoconjugate degradation in PBS and human plasma. Degradation of conjugate P/LLL(40%)TMZH(17%) in PBS and human plasma at 4° C. and 37° C. studied by relative changes in molecular size indicated by column retention times (% molecular weights) of SEC-HPLC and hydrodynamic diameter measured by a particle and molecular size analyzer ZETASIZER. 100% refers to the size at time zero.

Degradation of synthesized nanoconjugates was measured by SEC-HPLC and a particle and molecular size analyzer ZETASIZER in terms of molecular weight and hydrodynamic diameter respectively (data not shown). In PBS at 4° C., all synthesized nanoconjugates were stable maintaining over 85% of original $M_w$/size for more than 72 h. However, at temperatures 25° C. and especially at 37° C., substantial degradation was observed and $M_w$/size was reduced to 50% after 24-72 h in PBS. In human plasma at 37° C., conjugates degraded more rapidly compared with degradation in PBS and $M_w$/size was reduced by 50% after 12-36 h. As an example, degradation of conjugate P-LLL (40%)/TMZH(17%) is shown in FIG. 3.

Example 21

Membrane Destabilization

As an uncharged prodrug, TMZ can passively permeate the cells, where it is ultimately activated to the nucleic acid methylating methyldiazonium cation (33). Targeting of glioma cells by conjugated mAb would involve binding of the nanoconjugate delivery vehicle to overexpressed TfR and subsequent internalization into the endosomal system. In order to deliver the desired drug into the cytoplasm, disruption of the endosomal membrane would be essential. By systematic structure variation using PMLA as nanoplatform and membranes of artificial liposomes we have found LOEt and LLL substituting 40% of pendant PMLA carboxylates of the platform to be excellent candidates for endosomal membrane disruption (FIG. 2). Whereas the LLL unit was active only at pH 6-5.0 (FIG. 2a), resembling pH of late endosomes and lysosomes, the membrane disruption activity of the LOEt unit was pH-independent. The pH-dependence for LLL was referred to the ionization of the tripeptide carboxyl group. The $pK_a$ that governs ionization was shifted by conjugation with PMLA towards the neutral pH region due to the hydrophobic shielding by the multiple conjugated leucine side chains (Ding et al. "Poly(β-L-malic acid) with pendent leu-leu-leu-OH for endosome-routed cytoplasmic delivery". $14^{th}$ International Symposium on Recent Advances in Drug Delivery Systems, Salt Lake City, 2009, Abstract #91). FIG. 2 shows examples of liposome leakage caused by membrane disruption in the absence and presence of TMZH. LOEt was the more effective membrane disrupting agent (FIG. 2a). The loading by TMZH slightly increased the liposome leakage activity by LOEt and LLL units, but did not abolish the pH dependence for conjugate P/PEG(2%)LLL(40%)/TMZH(17%) (FIG. 2b). When TMZH was conjugated as in P/LLL(40%)/TMZH(17%), the leakage activity was improved and the pH-sensitivity disappeared (FIG. 2b). Most likely, this change was attributed to conjugation of TMZH with LLL-COOH residues thus eliminating the carboxylates that before gave rise to the observed pH dependence.

Example 22

Cell Viability Study

Figure 4:
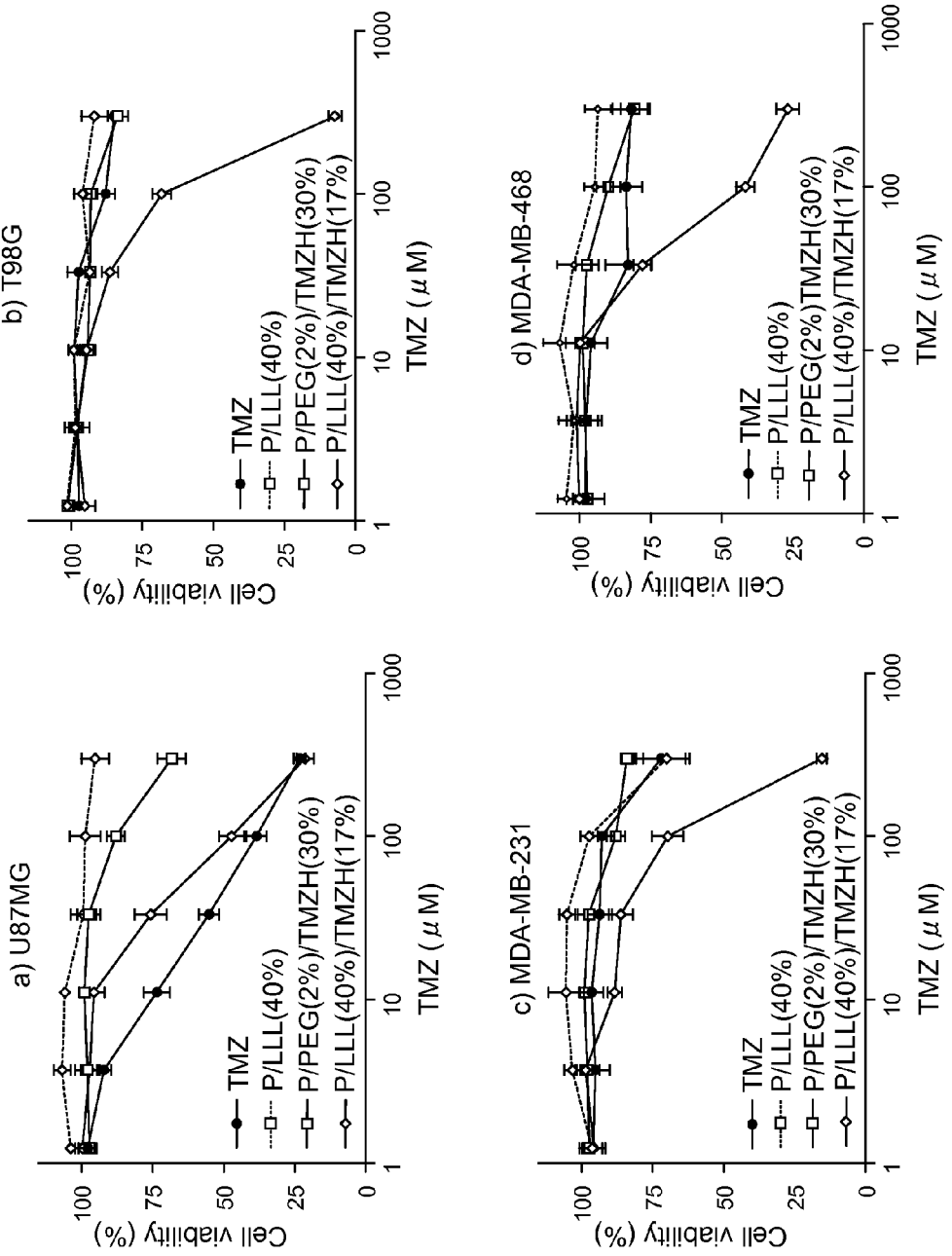
FIG. 4 depicts, in accordance with an embodiment herein, cell viability of nanoconjugate with LLL: Effects on cell viability of TMZ, P/LLL(40%), P/PEG(2%)/TMZH(30%) and P/LLL(40%)/TMZH(17%) on a) U87MG, b) T98G, c) MDA-MB-231 and d) MDA-MB-468 cells. Nanoconjugate P/LLL(40%) without drug was used as a control for the conjugate P/LLL(40%)/TMZH(17%) with drug and contains equivalent amount of polymer backbone. Nanoconjugate P/PEG(2%)/TMZH(30%) even with high loading of TMZH but without LLL endosome escape unit was only marginally effective. P/LLL(40%)/TMZH(17%) was the most effective nanoconjugate.
Figure 5:
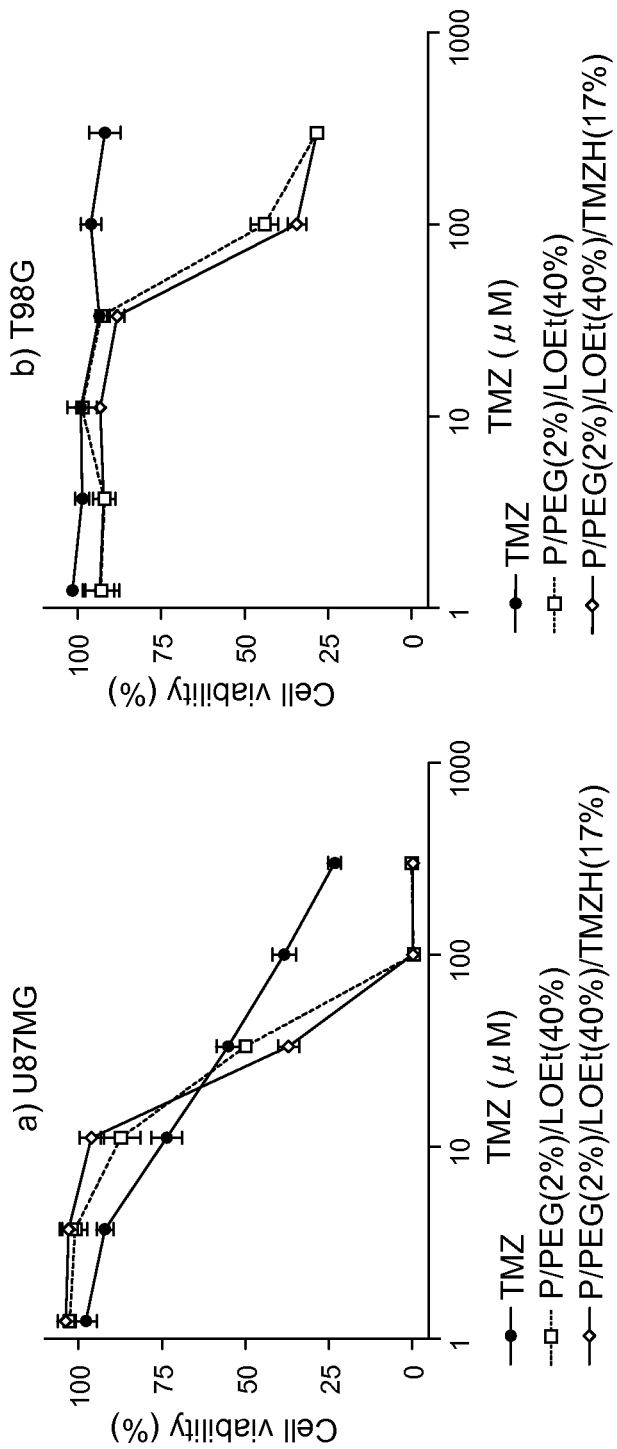
FIG. 5 depicts, in accordance with an embodiment herein, cell viability of nanoconjugate with LOEt: Effects on cell viability of TMZ, P/PEG(2%)/LOEt(40%) and P/PEG(2%)/LOEt(40%)/TMZH(17%) on a) U87MG and b) T98G cells. Nanoconjugate P/PEG(2%)/LOEt(40%) without drug was used as a control for the conjugate P/PEG(2%)/LOEt(40%)/TMZH(17%) with drug and contains equivalent amount of polymer backbone.

Effects of the nanoconjugates on cell viability were measured in order to investigate the influence of the delivery system on the TMZH prodrug activity and to test for cytotoxic activities of the delivery system itself in the absence of the prodrug. Results were compared with those for free TMZ and TMZH in a dose-dependent manner. P/PEG(2%)/TMZH(30%) had no significant effect on viability compared with free TMZ in the case of human glioma cell line U87MG (FIG. 4a), and it was ineffective on T98G, MDA-MB-231 and MDA-MB-468 cell lines (FIG. 4b-d). Conjugation of membrane disruption unit had pronounced effects on cell viability. Introduction of LOEt as a membrane disruption unit seemed to decrease cell viability significantly (FIG. 5); however, the decrease was apparently due to the nanoconjugate P/PEG(2%)/LOEt(40%) carrier itself and not by conjugated TMZH. As LOEt negatively affected cell viability in the observed concentration range, conjugates with this endosomal escape unit were not further considered. Importantly, introduction of LLL in the conjugate P/LLL (40%)/TMZH(17%) significantly decreased cell viability of all four cell cultures, gliomas U87MG and T98G, and breast cancer cell lines MDA-MB-231 and MDA-MB-468. In the same assay, free TMZ was inactive in all lines except U87MG. Conjugate P/LLL(40%) as a control had little or no effect on cell viability due to the absence of the prodrug (FIG. 4) and this was not changed by the addition of PEG$_{5000}$. The effect of coupling anti-TfR mAb to the nanoconjugate is shown in FIG. 6a. Whereas free TMZ had a stronger effect on U87MG cells than the nanoconjugates, these showed an increasing potency in the order P/PEG (2%)/LLL(40%)/TMZH(17%)/IgG(0.25%)<P/PEG(2%)/ LLL(40%)/TMZH(17%)<P/PEG(2%)/LLL(40%)/TMZH (17%)/HuTfR mAb(0.25%)<TMZ. In contrast, with the cell line MDA-MB-468, free TMZ was ineffective at all concentrations below 130 µM, whereas conjugates P/PEG(2%)/ LLL(40%)/TMZH(17%)/IgG(0.25%), P/PEG(2%)/LLL (40%)/TMZH(17%), P/PEG(2%)/LLL(40%)/TMZH(17%)/ HuTfR mAb(0.25%) showed significant reduction in viability and were almost equally effective.

Example 23

Confocal Microscopy

Figure 7:
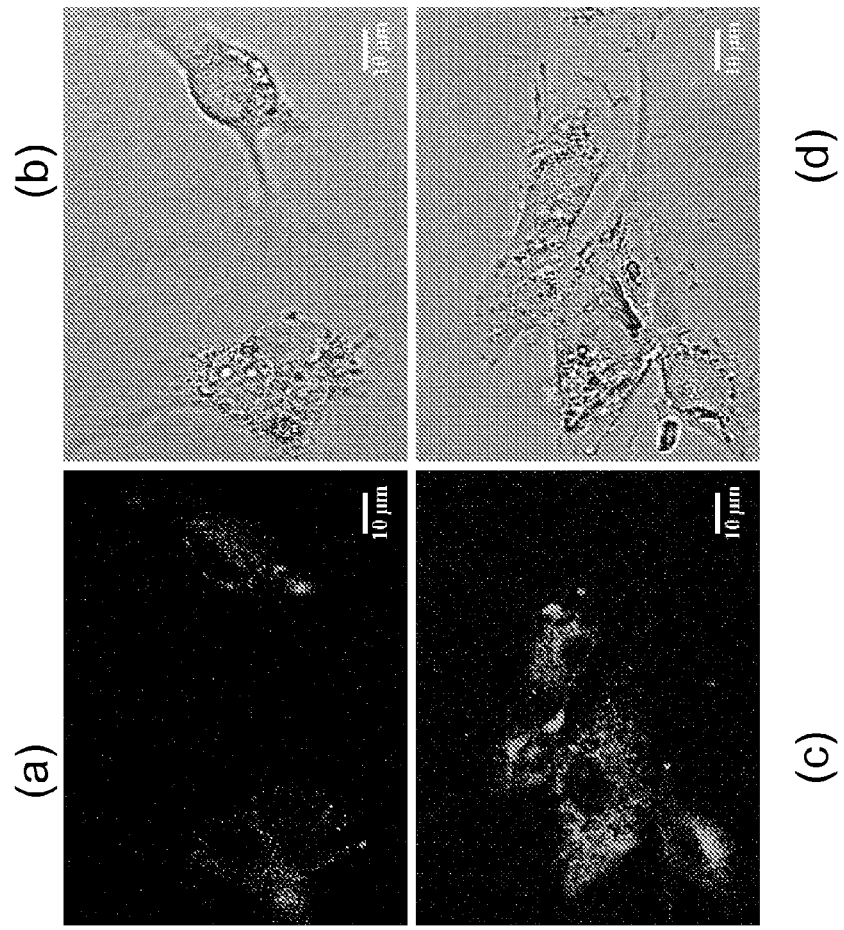
FIG. 7 depicts, in accordance with an embodiment herein, drug internalization into cultured human glioma U87MG cells by confocal microscopy: a) 1 h incubation with fluorescently labeled conjugate P/PEG(2%)/LLL(40%)TMZH (17%)/Alx680(1%). The location of conjugate is indicated by fluorescence; b) phase contrast; c) 1 h incubation with fluorescently labeled conjugate P/PEG(2%)/LLL(40%) TMZH(17%)/HuTfR mAb(0.25%)/Alx680(1%). The location of conjugate is indicated by fluorescence; d) phase contrast.
Figure 8:
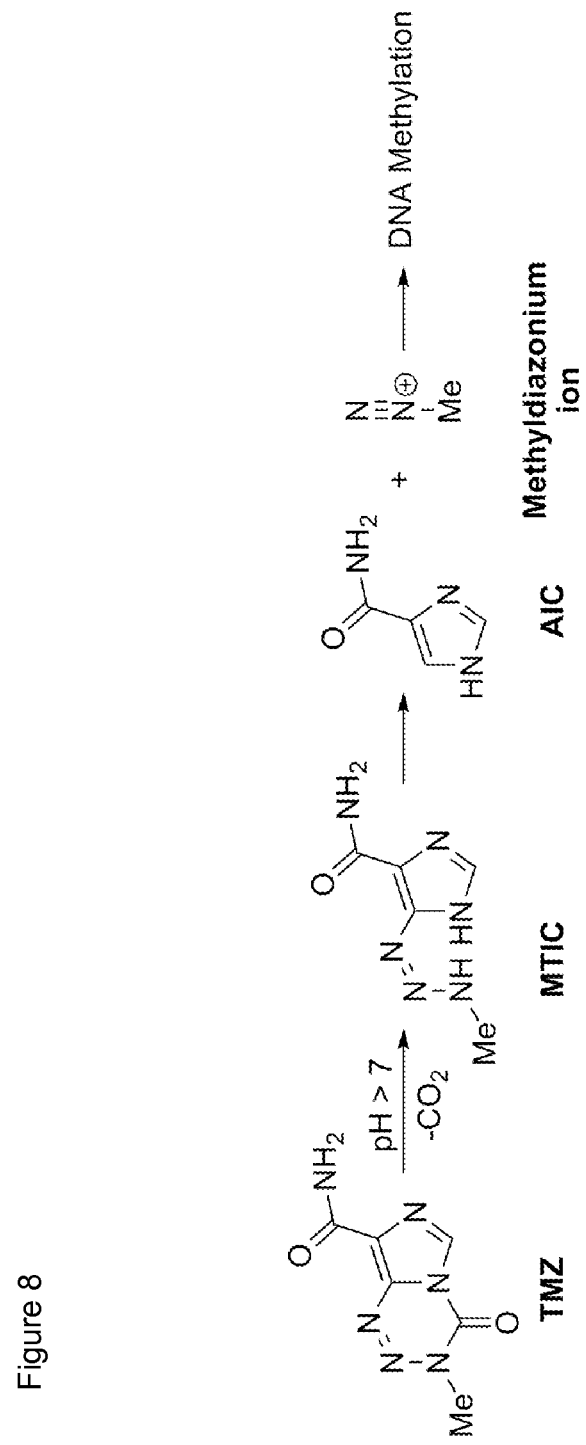
FIG. 8 depicts, in accordance with an embodiment herein, pH-dependent conversion of TMZ to metabolites, 5-(3-methyltriazen-1-yl)imidazole-4-carboxamide (MTIC), 4-amino-5-imidazole-carboxamide (AIC), methyldiazonium ion and DNA methylation (6).
Figure 9:
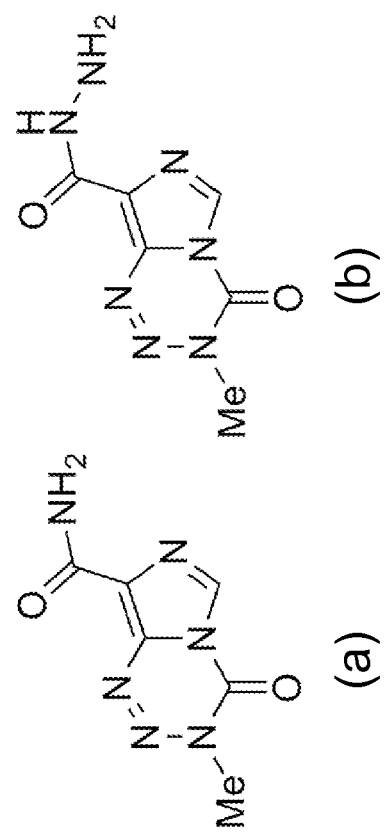
FIG. 9 depicts, in accordance with an embodiment herein, (a) temozolomide (TMZ) and (b) temozolomide hydrazide (TMZH).

The uptake of nanoconjugates was imaged by confocal microscopy following the appearance of fluorescence inside live human glioma U87MG cells (FIG. 7). Uptake into vesicles was observed for both conjugates P/PEG(2%)/LLL (40%)/TMZH(17%) and P/PEG(2%)/LLL(40%)/TMZH (17%)/HuTfR mAb(0.25%) labeled with Alex680. At a fixed instrument setting, the intensity and the number of vesicles was higher for the actively targeting conjugate with TfR mAb than for the conjugate lacking the antibody. It can be concluded that the nanodrugs were internalized most likely by receptor-mediated endocytosis and possibly also by pinocytotic pathways.

Example 24

Discussion

Orally applied TMZ to treat human gliomas has the potency to be distributed all over the entire organism. After penetration of the lipophilic prodrug through membranes into the cytoplasm of recipient cells it will be activated by the hydrolytic mechanism described herein. The active drug is then ready to methylate proteins and especially DNA, guanine at N7 position, followed by methylation of adenine at the 03 position and of guanine at the 06 position (33). Failure of repair will drive these cells into apoptosis. Hydrolytic activation of the prodrug at sites other than the cytoplasm is inefficient due to the fact that the cationic methyl diazonium like any other charged molecule cannot passively penetrate membranes.

The inventors have succeeded to conjugate TMZ via the hydrazide bond to the highly negatively charged PMLA that renders the prodrug no longer diffusible through membranes. As a consequence, the active methyl diazonium cation can only be generated from the nanodrug. Free passive diffusion of the PMLA conjugate into recipient cells is highly unlikely because of its high negative charge, and generation of active drug outside the cytoplasm would not be effective due to its own intrinsic charge. Therefore, the nanodrug can only give rise to nucleic acid methylation if it is internalized into the cytoplasm of recipient cells. The results in FIG. 7 show that drug uptake follows most likely receptor-mediated endocytosis and possibly pinocytotic pathways of the conjugates P/PEG(2%)/LLL(40%)/TMZH (17%)/HuTfR mAb (0.25%) and P/PEG(2%)/LLL(40%)/ TMZH(17%) that were labeled with Alex680. Without exiting from the endosome into the cytoplasm, drug activation would be still ineffective due to the vesicle membrane barrier, explaining why conjugate P/PEG(2%)/TMZH(30%) without any endosome disruption unit did not affect cell viability (FIG. 4). Moreover, maturing endosomes undergo acidification rendering drug activation unlikely, because this requires neutral or higher pH. If the nanodrug carries the membrane disrupting LLL device as in the case of the above conjugates, it could enter the cytoplasm, and there, by virtue of physiological pH, the prodrug could be converted into its active form and methylate DNA.

To satisfy the above mechanism, the inventors synthesized the nanodrug carrying targeting TfR antibodies, endosome escape unit, and the prodrug. The results in FIGS. 4 and 6 show the delivery and prodrug activation to follow the anticipated mechanism. The effect of the targeting HuTfR mAb was observed in the case of human glioma U87MG cells. A significant reduction of viability is seen in the presence of the endosome escape unit LLL for all cell lines shown in FIGS. 4 and 6. This in agreement with the stringent requirement for endosome escape in the prodrug delivery mechanism.

Whereas glioma U87MG cells responded to treatment with free TMZ, cell viability of glioma T98G and breast cancer MDA-MB-231 and MDA-MB-468 cells did not change. These cell lines are known to be TMZ resistant (32-34). In the case of T98G cells, resistance has been referred to overproduction of 06-methyl guanine methyltransferase (MGMT) (32), that of MDA-MB-231 cells has been associated with unbalanced expression of DNA glycosylase and DNA polymerase expression (34), and the mechanism of resistance is not known for MDA-MB-468 cells. If indeed the lack of response to free TMZ for T98G, MDA-MB-231 and MDA-MB-468 in FIG. 4 referred to TMZ resistance, the observed significant decrease of cell viability (FIGS. 4 and 6) showed that the nanoconjugates P/PEG(2%)/LLL(40%)/TMZH(17%), P/LLL(40%)/TMZH (17%)/HuTfR mAb(0.25%) and P/LLL(40%)/TMZH(17%)/ IgG(0.25%) had the ability to overcome the resistance. On the basis of their unique results, conjugates P/PEG(2%)/LLL (40%)/TMZH(17%) and P/LLL(40%)/TMZH(17%)/HuTfR mAb(0.25%) were designed as lead compounds with potential for treatment of glial tumors in vivo.

The drug delivery system offers a biodegradable, non-toxic, and non-immunogenic scaffold obtained from a biological source, thus opening an avenue for drug delivery without the danger of liver storage disease. Conjugation of TMZH to this platform has been challenging because of the sensitivity of the prodrug to neutral and alkaline pH. Nonetheless, syntheses of TMZ nanodrugs have been worked out to be readily achievable and highly reproducible. The solution properties such as solubility and absence of aggregation, size in the nanometer range, and slightly negative zeta potential are favorable for drug delivery (35, 36). One of the lead conjugates contains PEG$_{5000}$, which minimizes enzymatic nanodrug degradation and clearance by the reticuloendothelial system (37). The nanodrugs are stable in human plasma over several hours, and the range of half-life for active drug formation has increased several-fold over that of free TMZ by conjugation to the PMLA platform. The increased half-life of conjugated TMZ favors an efficient delivery of functional prodrug in vivo. On the basis of the data, the following in vivo scenario is likely: After I.V. application, the nanodrug will be accumulated in the interstitial space of malignant glioma by EPR effect (19) and/or active mAb targeting of overexpressed TfR on vascular endothelium next to the tumor (21). From the interstitium, the nanodrug will enter the endosomal system of tumor cells and become activated in the cytoplasm after endosomal escape. Accumulation in the tumor by EPR effect and especially, active mAb targeting provides efficiency of tumor treatment with minimal side effects for healthy tissue.

Example 25

TABLE 1

Physicochemical properties of the conjugates and half-lives of TMZ

| Conjugates | Hydrodynamic diameter (nm)[a] | Zeta potential (mV)[b] | Half-life of TMZ (h)[c] |
|---|---|---|---|
| TMZ | n.d. | n.d. | 1.80 (±0.1)[d] |
| TMZH | n.d. | n.d. | 1.98 (±0.1) |
| PMLA | 6.6 (±0.1) | 22.9 (±1.7) | n.d. |
| P/PEG (2%)/TMZH (30%)[e] | 7.8 (±0.4) | 16.1 (±1.2) | 7.10 (±0.2) |
| P/PEG (2%)/LOEt (40%)/TMZH (17%) | 8.5 (±0.4) | −6.7 (±0.2) | 4.92 (±0.3) |
| P/PEG (2%)/LLL (40%)/TMZH (17%) | 6.9 (±1.3) | 11.5 (±1.8) | 6.25 (±0.2) |
| P/LLL (40%)/TMZH (17%) | 6.5 (±0.2) | 17.7 (±2.1) | 7.34 (±0.2) |
| P/PEG (2%)/LLL (40%)/TMZH (17%))/HuTfR mAb (0.25%) | 14.8 (±2.1) | −6.3 (±1.7) | n.d. |

[a]Hydrodynamic diameter at 25° C. measured in PBS at a concentration of 2 mg/ml;
[b]$\zeta$ potential at 25° C. in aqueous solution of 10 mM NaCl at 150 V;
[c]half-life measured at physiological pH in PBS at 37° C.;
[d]Mean values and S.D. for three independent measurements;
[e]percentage refers to total number (100%) of pendant carboxyl groups in unsubstituted PMLA;
n.d., not done.

Example 26

Conclusions

For the purpose of targeting TMZ to human glioma, TMZH was conjugated to PMLA platform, which was equipped with anti-human TfR antibodies for tumor cell targeting by receptor mediated endocytosis; and pH-dependent LLL for endosome escape. The lead compounds P/PEG (2%)/LLL(40%)/TMZH(17%)/HuTfR mAb(0.25%) and P/LLL(40%)/TMZH(17%) showed significant reduction in tumor cell viability of both human glioma and human breast cancer cell lines. Cell viability was significantly reduced in cases of TMZ-resistant cell lines where free TMZ had no effect.

Example 27

Efficacy of Delivery System In Vivo

After numerous in vitro screening, it was important to investigate the efficacy of delivery system in vivo. To prove the concept, subcutaneous model was used using human glioma U87MG cell line. $3 \times 10^6$ cells were inoculated in nude mice and tumors were formed. Conjugate P/PEG(2%)/LLL(40%)/TMZ(15%) was chosen for the in vivo study and was synthesized following a similar procedure described for conjugate P/PEG(2%)/LOEt(40%)/TMZH(17%).

After inoculation of human glioma cells in nude mice, all the animals were randomized as the average tumor volume reached about 125 mm$^3$ (day 28 after inoculation). Animals were divided in two different groups as shown in Table 2. Nanoconjugates are highly soluble in aqueous solutions and were dissolved in PBS prior to the administration. Drug was administered intravenously (I.V.) for five consecutive days at a temozolomide concentration of 4 mg/kg. Tumor volume was measured 3 times a week and all the animals were euthanatized on day 37.

TABLE 2

Treatment plan for tumor bearing mice with temozolomide nanoconjugate.

| Group 1 | Group 2 |
|---|---|
| n = 4 | n = 4 |
| PBS | P-PEG(2%)LLL(40%)/TMZ (15%) |
| IV for 5 days for 5 days | 4 mg/kg (TMZ concentration) |
| | 65 mg/kg (nanoconjugate concentration) |
| | IV for 5 days |

Figure 12:
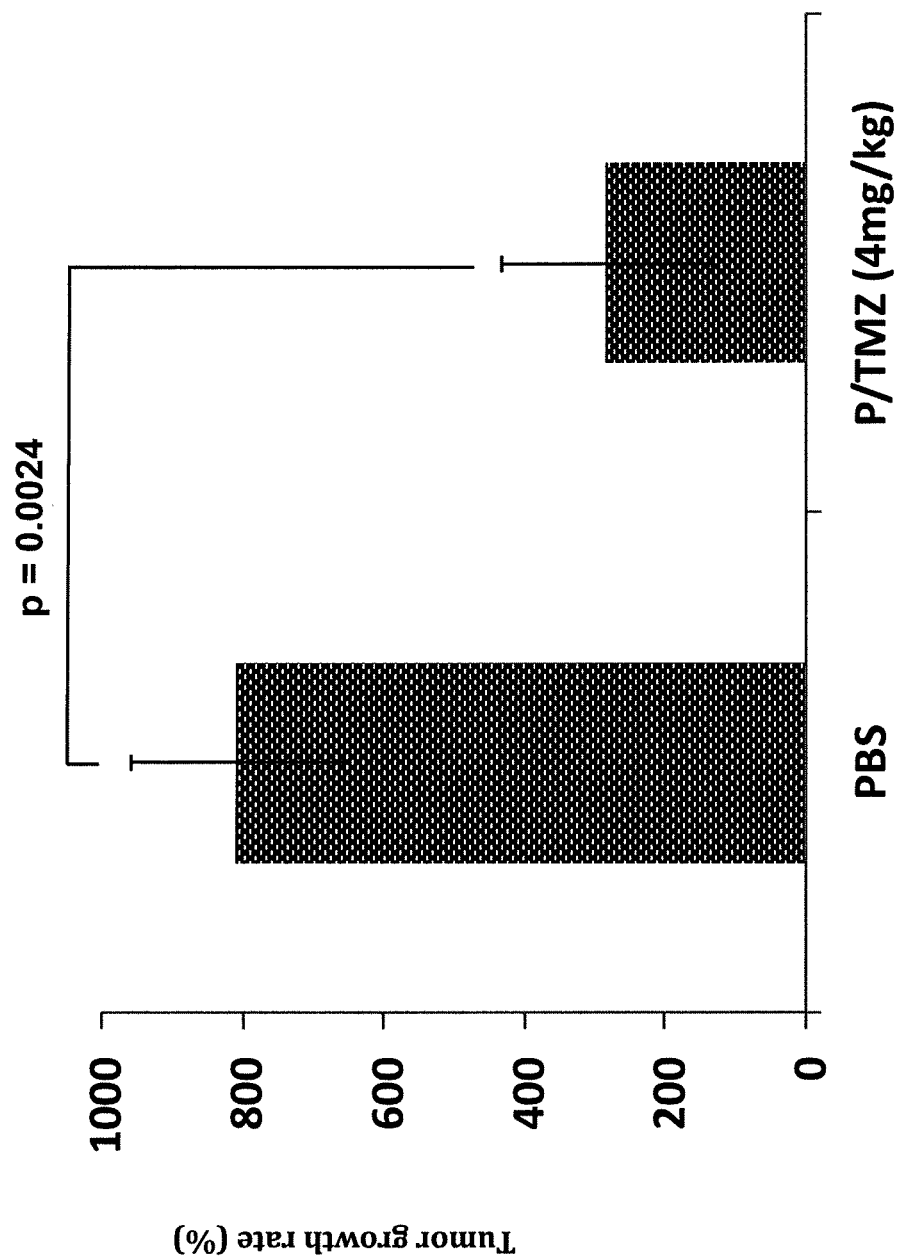
FIG. 12 depicts, in accordance with an embodiment herein, comparison of tumor growth rate between treated and untreated animals.
Figure 13:
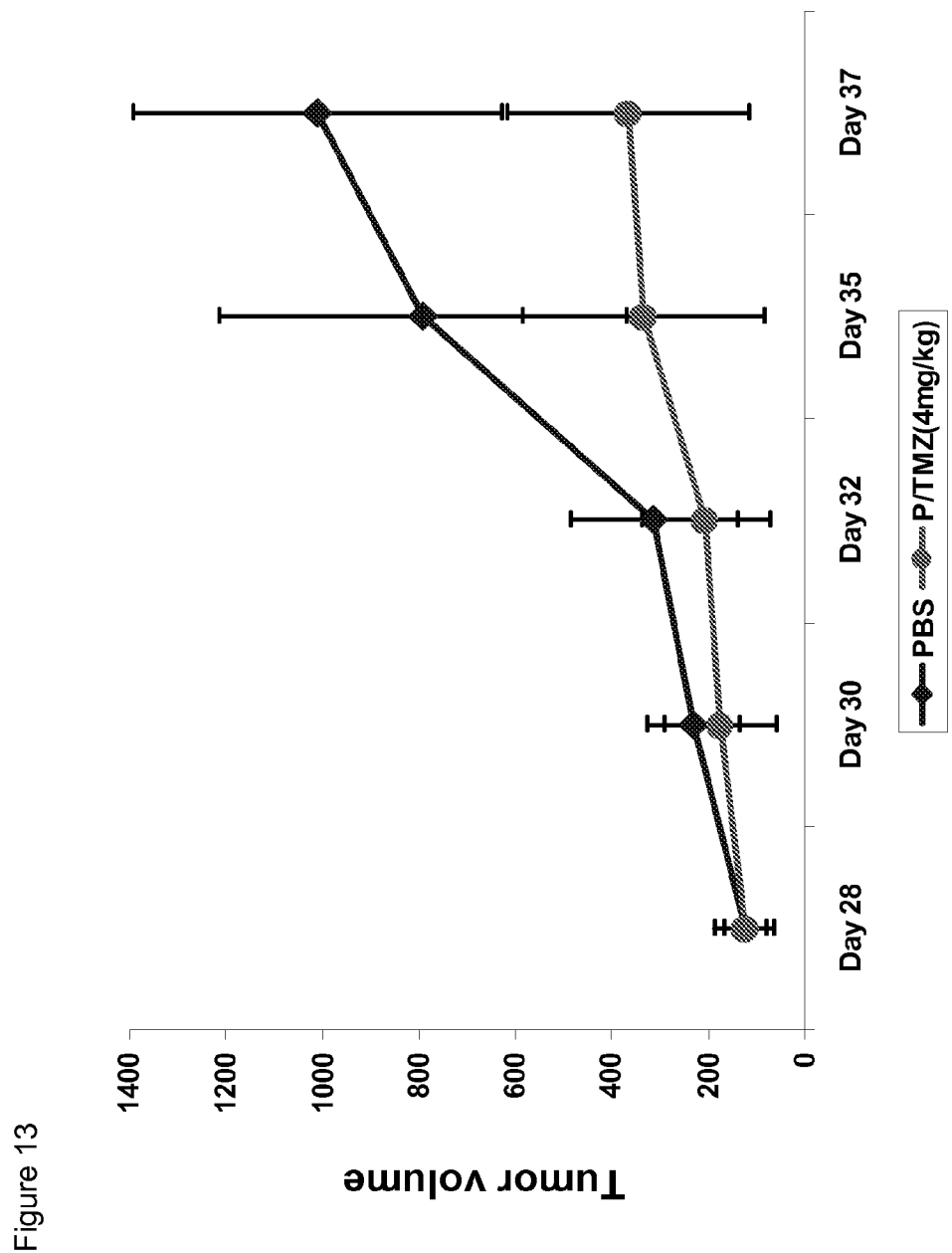
FIG. 13 depicts, in accordance with an embodiment herein, comparison of tumor volume between treated and untreated animals.

Treatment of animals with P/PEG(2%)/LLL(40)/TMZ (15%) {With 4 mg/kg of TMZ concentration} showed significant tumor growth inhibition compared with PBS treated animals. (p=0.0024, calculated from tumor growth rate as shown herein in FIG. 12). Temozolomide conjugate P/PEG(2%)/LLL(40)/TMZ(15%) at lower concentration (1 mg/kg of TMZ) did not achieve the desired effect. FIG. 13 illustrates the total tumor volume of different treatment groups.

Temozolomide nanoconjugate synthesized using polymalic acid as a platform significantly inhibited the tumor growth and proved its efficacy in vivo. Even without any active targeting, the nanoconjugate was effective.

Example 28

Temozolomide (TMZ) Dosage

FDA-approved dosage to treat patients in clinic using oral administration:
Newly Diagnosed High Grade Glioma:
75 mg/m$^2$ (corresponds to 2.3 mg/kg) daily p.o. for 42 days combined with focal radiotherapy followed by maintenance temozolomide for six cycles.
Maintenance Phase:
Cycle 1: 150 mg/m$^2$ (corresponds to 4.6 mg/kg) p.o. daily followed by 23 days without treatment.
Cycle 2 to 6: 200 mg/m$^2$ (corresponds to 6.15 mg/kg) p.o. daily followed by 23 days without treatment if toxicity does not occur.

In conjunction with various drug delivery systems described herein, TMZ can be administered via I.V. injection. As described herein, the inventors used mouse xenograft (U87MG, human glioma): 4 mg/kg intravenous injections for 5 consecutive days. As a result, the drug is less toxic because the direct tumor delivery and drug concentration in the tumor site is higher than after oral drug is administrated. TMZ covalently attached on polymer overcomes drug resistance.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. D. N. Louis, H. Ohgaki, O. D. Wiestler, W. K. Cavenee, P. C. Burger, A. Jouvet, B. W. Scheithauer, and P. Kleihues. The 2007 WHO classification of tumours of the central nervous system. Acta Neuropathol. 114:97-109 (2007).
2. 2009 CBTRUS Statistical Report: Primary Brain and Central Nervous System Tumors Diagnosed in the United States in 2004-2005. http://www.cbtrus.org/reports/2009-NPCR-04-05/CBTRUS-NPCR2004-2005-Report-.pdf (accessed Nov. 17, 2009).
3. A. R. Asthagiri, N. Pouratian, J. Sherman, G. Ahmed, and M. E. Shaffrey. Advances in brain tumor surgery. Neurol Clin. 25:975-1003 (2007).
4. W. Stummer, U. Pichlmeier, T. Meinel, O. D. Wiestler, F. Zanella, and H. J. Reulen. Fluorescence-guided surgery with 5-aminolevulinic acid for resection of malignant glioma: a randomised controlled multicentre phase III trial. Lancet Oncol. 7:392-401 (2006).
5. M. Lacroix, D. Abi-Said, D. R. Fourney, Z. L. Gokaslan, W. Shi, F. DeMonte, F. F. Lang, I. E. McCutcheon, S. J. Hassenbusch, E. Holland, K. Hess, C. Michael, D. Miller, and R. Sawaya. A multivariate analysis of 416 patients with glioblastoma multiforme: prognosis, extent of resection, and survival. J. Neurosurg. 95:190-198 (2001).
6. J. Arrowsmith, S. A. Jennings, D. A. Langnel, R. T. Wheelhouse, and M. F. Stevens. Antitumour imidazotetrazines. Part 39 synthesis of bis(imidazotetrazine)s with saturated spacer groups. J Chem Soc Perkin Trans 1. 24:4432-4438 (2000).
7. R. Stupp, W. P. Mason, M. J. van den Bent, M. Weller, B. Fisher, M. J. Taphoorn, K. Belanger, A. A. Brandes, C. Marosi, U. Bogdahn, J. Curschmann, R. C. Janzer, S. K. Ludwin, T. Gorlia, A. Allgeier, D. Lacombe, J. G. Cairncross, E. Eisenhauer, and R. O. Mirimanoff. Radiotherapy plus concomitant and adjuvant temozolomide for glioblastoma. N Engl J. Med. 352:987-996 (2005).
8. N. Auger, J. Thillet, K. Wanherdrick, A. Idbaih, M. E. Legrier, B. Dutrillaux, M. Sanson, and M. F. Poupon. Genetic alterations associated with acquired temozolomide resistance in SNB-19, a human glioma cell line. Mol Cancer Ther. 5:2182-2192 (2006).
9. C. C. Chen, K. T. Kahle, K. Ng, M. Nitta, and A. D. Andrea. Of *escherichia coli* and man: understanding glioma resistance to temozolomide therapy. In E. G. Meir (eds.), CNS Cancer, Humana Press, Atlanta, 2009, pp 679-711.
10. G. J. Kitange, B. L. Carlson, M. A. Schroeder, P. T. Grogan, J. D. Lamont, P. A. Decker, W. Wu, C. D. James, and J. N. Sarkaria. Induction of MGMT expression is associated with temozolomide resistance in glioblastoma xenografts. Neuro Oncol. 11:281-291 (2009).
11. R. Satchi-Fainaro, M. Puder, J. W. Davies, H. T. Tran, D. A. Sampson, A. K. Greene, G. Corfas, and J. Folkman. Targeting angiogenesis with a conjugate of HPMA copolymer and TNP-470. Nat. Med. 10:255-261 (2004).
12. R. Duncan. The dawning era of polymer therapeutics. Nat Rev Drug Discov. 2:347-360 (2003).
13. S. V. Vinogradov, E. V. Batrakova, S. Li, and A. V. Kabanov. Mixed polymer micelles of amphiphilic and cationic copolymers for delivery of antisense oligonucleotides. J Drug Target. 12:517-526 (2004).
14. A. V. Kabanov, E. V. Batrakova, S. Sriaclibhatla, Z. Yang, D. L. Kelly, and V. Y. Alakov. Polymer genomics: shifting the gene and drug delivery paradigms. J Control Release. 101:259-271 (2005).
15. D. Peer, J. M. Karp, S. Hong, O. C. Farokhzad, R. Margalit, and R. Langer. Nanocarriers as an emerging platform for cancer therapy. Nat. Nanotechnol. 2:751-760 (2007).
16. M. Ferrari. Cancer nanotechnology: opportunities and challenges. Nat Rev Cancer. 5:161-171 (2005).
17. A. Nori, and J. Kopecek. Intracellular targeting of polymer-bound drugs for cancer chemotherapy. Adv Drug Deliv Rev. 57:609-636 (2005).
18. R. Duncan, M. J. Vicent, F. Greco, and R. I. Nicholson. Polymer-drug conjugates: towards a novel approach for the treatment of endrocine-related cancer. Endocr Relat Cancer. 12:S189-S199 (2005).
19. H. Maeda, J. Fang, T. Inutsuka, and Y. Kitamoto. Vascular permeability enhancement in solid tumor: various factors, mechanisms involved and its implications. Int Immunopharmacol. 3:319-328 (2003).
20. M. Fujita, B. S. Lee, N. M. Khazenzon, M. L. Penichet, K. A. Wawrowsky, R. Patil, H. Ding, E. Holler, K. L. Black, and J. Y. Ljubimova. Brain tumor tandem targeting using a combination of monoclonal antibodies attached to biopoly(b-L-malic acid). J Control Release. 122:356-363 (2007).
21. B. S. Lee, M. Fujita, N. M. Khazenzon, K. A. Wawrowsky, S. Wachsmann-Hogiu, D. L. Farkas, K. L. Black, J. Y. Ljubimova, and E. Holler. Polycefin, a new prototype of a multifunctional nanoconjugate based on poly(b-L-malic acid) for drug delivery. Bioconjug Chem. 17:317-326 (2006).
22. E. Segal, and R. Satchi-Fainaro. Design and development of polymer conjugates as anti-angiogenic agents. Adv Drug Deliv Rev. 61:1159-1176 (2009).
23. S. Brem, B. Tyler, K. Li, G. Pradilla, F. Legnani, J. Caplan, and H. Brem. Local delivery of temozolomide by biodegradable polymers is superior to oral administration in a rodent glioma model. Cancer Chemother Pharmacol. 60:643-650 (2007).
24. U. Akbar, T. Jones, J. Winestone, M. Michael, A. Shukla, Y. Sun, and C. Duntsch. Delivery of temozolomide to the tumor bed via biodegradable gel matrices in a novel model of intracranial glioma with resection. J Neurooncol. 94:203-212 (2009).
25. L. X. Zhao, J. L. Wang, X. P. Dai, Y. F. Wang, and Z. Z. Ji. Synthesis and antitumour activities of 3-substituted 4-oxo-3H-imidazo[5,1-d][1,2,3,5]tetrazine-8-carboxylic acids and their derivatives. Chin J Med. Chem. 11:263-269 (2001).
26. E. Holler, Poly(malic acid) from natural sources. In N. P. Cheremisinoff (eds.), Handbook of Engineering Polymeric Materials, Marcel Dekker, New York, 1997, pp. 93-103.
27. J. Carlsson, H. Drevin, and R. Axen. Protein thiolation and reversible protein-protein conjugation. N-Succinimidyl 3-(2-pyridyldithio)propionate, a new heterobifunctional reagent. Biochem J. 173:723-737 (1978).
28. J. Y. Ljubimova, M. Fujita, A. V. Ljubimov, V. P. Torchilin, K. L. Black, and E. Holler. Poly(malic acid) nanoconjugates containing various antibodies and oligonucleotides for multitargeting drug delivery. Nanomedicine. 3:247-265 (2008).
29. I. O. f. S. (ISO). Methods for Determination of Particle Size Distribution Part 8: Photon Correlation Spectroscopy, International Standard ISO 13321, 1996.
30. P. C. Hiemenz, Light scattering by polymer solutions, In P. C. Hiemenz (eds.), Polymer Chemistry: The Basic Concepts, Marcel Decker, New York, 1984, pp. 659-661.
31. F. N. Fu, and B. R. Singh. Calcein permeability of liposomes mediated by type A botulinum neurotoxin and its light and heavy chains. J Protein Chem. 18:701-707 (1999).
32. T. J. Mosmann. Rapid colorimetric assays for cellular growth and survival: application to proliferation and cytotoxicity assays. Immunol Methods. 65:55-63 (1983).
33. H. S. Friedman, T. Kerby, and H. Calvert. Temozolomide and treatment of malignant glioma. Clin Cancer Res. 6:2585-2597 (2000).
34. R. N. Trivedi, X. H. Wang, E. Jelezcova, E. M. Goellner, J. B. Tang, and R. W. Sobol. Human methyl purine DNA glycosylase and DNA polymerase b expression collectively predict sensitivity to temozolomide. Mol. Pharmacol. 74:505-516 (2008).
35. A. E. Nel, L. Madler, D. Velegol, T. Xia, E. M. Hoek, P. Somasundaran, F. Klaessig, V. Castranova, and M. Thompson. Understanding biophysicochemical interactions at the nano-bio interface. Nat. Mater. 8:543-557 (2009).
36. M. R. Lorenz, V. Holzapfel, A. Musyanovych, K. Nothelfer, P. Walther, H. Frank, K. Landfester, H. Schrezenmeier, and V. Mailander. Uptake of functionalized, fluorescent-labeled polymeric particles in different cell lines and stem cells. Biomaterials. 27:2820-2828 (2006).
37. D. E. Owens, and N. A. Peppas. Opsonization, biodistribution, and pharmacokinetics of polymeric nanoparticles. Int J. Pharm. 307:93-102 (2006).

What is claimed is:

1. A composition comprising a polymalic acid-based scaffold, an endosomal membrane disrupting unit and temozolomide, wherein the temozolomide is covalently attached to the polymalic acid via a hydrazide bond, and wherein the membrane disrupting unit comprises trileucine or leucine ethyl ester.

2. The composition of claim 1, wherein the polymalic acid comprises poly(β-L-malic acid).

3. The composition of claim 1, further comprising a targeting moiety.

4. The composition of claim 3, wherein the targeting moiety is an antibody.

5. The composition of claim 3, wherein the targeting moiety comprises an anti-TfR antibody.

6. The composition of claim 1, further comprising polyethylene glycol.

7. A polymalic acid-based scaffold comprising:

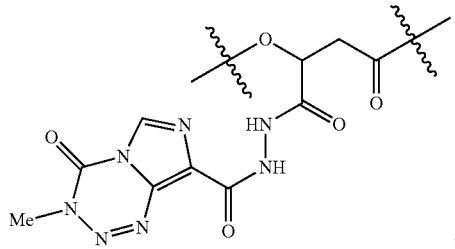

and one or more of:

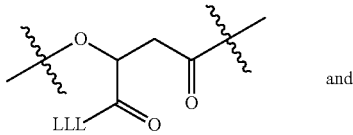

and

-continued

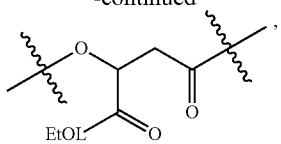

or a pharmaceutically acceptable salt thereof, wherein -LLL is —NH-Leu-Leu-LeuOH and -LOEt is —NH-LeuOEt.

8. The polymalic acid-based scaffold of claim 7, further comprising:

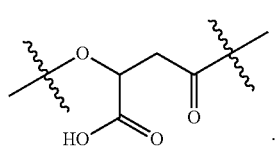 [SMILES: *OC(CC(*)=O)C(=O)O]

9. The polymalic acid-based scaffold of claim 7, comprising:

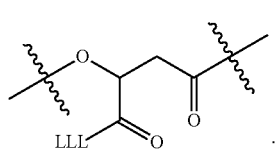

10. The polymalic acid-based scaffold of claim 7, comprising:

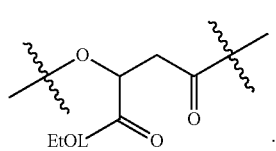

11. The polymalic acid-based scaffold of claim 7, further comprising:

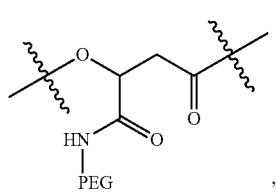

wherein PEG is polyethylene glycol.

12. The polymalic acid-based scaffold of claim 7, further comprising:

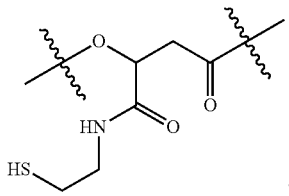

13. The polymalic acid-based scaffold of claim 8, comprising:

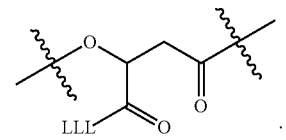

14. The polymalic acid-based scaffold of claim 13, further comprising:

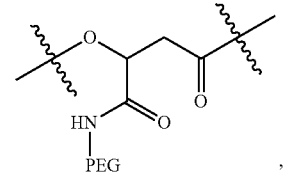

wherein PEG is polyethylene glycol.

15. A pharmaceutical composition comprising a therapeutically effective amount of the polymalic acid-based scaffold of claim 7 and a pharmaceutically acceptable excipient.

16. The pharmaceutical composition of claim 15, wherein the composition is formulated for intravenous administration.

17. A method of treating cancer in a subject, the method comprising administering to a subject in need thereof a therapeutically effective amount of the polymalic acid-based scaffold of claim 7.

18. The method of claim 17, wherein the cancer is selected from a brain cancer and a glioma.

* * * * *